US012774282B2

(12) United States Patent
Zeng et al.

(10) Patent No.: US 12,774,282 B2
(45) Date of Patent: Oct. 27, 2026

(54) OXASPIRO SUBSTITUTED PYRROLOPYRAZOLE DERIVATIVE, INTERMEDIATE THEREOF, AND PREPARATION METHOD THEREFOR

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Taizhou (CN)

(72) Inventors: Zhenya Zeng, Shanghai (CN); Chao Kan, Shanghai (CN); Qingfu Gao, Shanghai (CN); Yixiao Feng, Shanghai (CN); Bo Wu, Shanghai (CN); Xingsong Zhang, Shanghai (CN); Youhong Ma, Shanghai (CN); Kejun Sun, Shanghai (CN)

(73) Assignees: SHANGHAI HAIYAN PHARMACEUTICAL TECHNOLOGY CO., LTD., Shanghai (CN); YANGTZE RIVER PHARMACEUTICAL GROUP CO., LTD, Taizhou (CN)

( * ) Notice: Subject to any disclaimer, the term of this patent is extended or adjusted under 35 U.S.C. 154(b) by 603 days.

(21) Appl. No.: 18/259,743

(22) PCT Filed: Dec. 29, 2021

(86) PCT No.: PCT/CN2021/142283

§ 371 (c)(1),
(2) Date: Jun. 28, 2023

(87) PCT Pub. No.: WO2022/143715

PCT Pub. Date: Jul. 7, 2022

(65) Prior Publication Data

US 2024/0109895 A1 Apr. 4, 2024

(30) Foreign Application Priority Data

Dec. 29, 2020 (CN) ........................ 202011598623.5

(51) Int. Cl.
*C07D 487/04* (2006.01)

(52) U.S. Cl.
CPC .................................. *C07D 487/04* (2013.01)

(58) Field of Classification Search
CPC .................................................... C07D 487/04
See application file for complete search history.

(56) References Cited

FOREIGN PATENT DOCUMENTS

| | | | | | |
|---|---|---|---|---|---|
| CN | 109206417 | A | | 1/2019 | |
| CN | 109516982 | A | | 3/2019 | |
| JP | 2020534294 | A | | 11/2020 | |
| JP | 2020535177 | A | | 12/2020 | |
| WO | WO2011027081 | A2 | | 3/2011 | |
| WO | WO2014041349 | A1 | | 3/2014 | |
| WO | WO2017106547 | A1 | | 6/2017 | |
| WO | WO-2019062804 | A1 | * | 4/2019 | ........... C07D 311/96 |
| WO | WO2019144805 | A1 | | 8/2019 | |
| WO | WO2019205983 | A1 | | 10/2019 | |
| WO | WO2021143801 | A1 | | 7/2021 | |
| WO | WO2021143803 | A1 | | 7/2021 | |
| WO | WO-2023284775 | A1 | * | 1/2023 | ......... A61K 31/4439 |

OTHER PUBLICATIONS

WO 2023284775 A1 Machine Translation (Year: 2023).*
WO2019062804A1 Machine Translation (Year: 2019).*
Office Action fro Chinese Application No. 202180071002.8, Dated Dec. 13, 2024, 19 pages.
Search Report for European Application No. 21914449.0, Dated Dec. 6, 2024, 10 pages.
Office Action for Japanese Application No. 2023-540120, Dated Oct. 8, 2024, 6 pages.
International Search Report and Written Opinion mailed Mar. 29, 2022 in International Application No. PCT/CN2021/142283, 20 pages.
Office Action for Japanese Application No. 2023-540120, Dated Jun. 24, 2024, 91 pages.

* cited by examiner

*Primary Examiner* — Sarah Pihonak
*Assistant Examiner* — Mikhail O'donnel Robinson
(74) *Attorney, Agent, or Firm* — Lee & Hayes, P.C.

(57) ABSTRACT

An oxaspiro substituted pyrrolopyrazole derivative, an intermediate thereof, and a preparation method therefor.

20 Claims, 1 Drawing Sheet

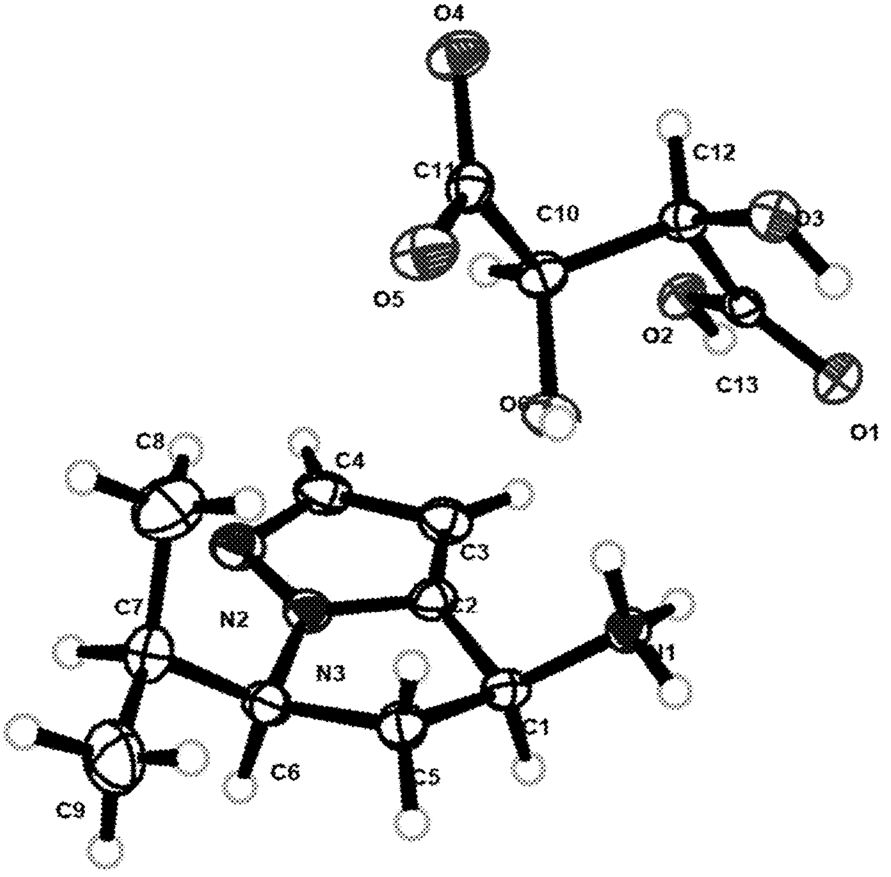

OXASPIRO SUBSTITUTED PYRROLOPYRAZOLE DERIVATIVE, INTERMEDIATE THEREOF, AND PREPARATION METHOD THEREFOR

CROSS REFERENCE TO RELATED APPLICATIONS

This application is a U.S. National Phase of International Application No. PCT/CN2021/142283, filed Dec. 29, 2021, which claims the benefit of Chinese application Ser. No. 202011598623.5, filed Dec. 29, 2020, both of which are incorporated herein by reference in their entirety.

FIELD

The present disclosure relates to the field of organic chemical synthesis, and particularly, to oxaspiro substituted pyrrolopyrazole derivatives, intermediates thereof, and preparation methods therefor.

BACKGROUND

Opioid receptors are an important class of G protein-coupled receptors (GPCRs), to which endogenous opioid peptides and opioid drugs bind. Endogenous opioid peptides are opioid-like active substances that are naturally produced in mammals, and the known endogenous opioid peptides are broadly classified into enkephalins, endorphins, dynorphins, and neoendorphins. Corresponding opioid receptors, namely μ (MOR) receptor, δ (DOR) receptor, κ (KOR) receptor, and the like, are present in the central nervous system. Studies have found that an analgesic effect of endogenous opioid peptides mainly depends on the expression level of opioid receptors, the targets on which analgesic effects of opioid drugs as well as endogenous opioid peptides act.

MOR agonists with different structures have been reported and methods for preparing these compounds have also been disclosed, including WO2017106547, WO2017063509, WO2012129495, WO2017106306, etc. It is of great significance for pharmaceutical and industrial production to develop high-efficient, low-cost, easy-to-scale-up and reproducible synthetic processes for new MOR agonists with better activity and selectivity.

SUMMARY

An object of the present disclosure is to further develop intermediates suitable for industrial production based on the developed novel MOR agonists and methods for preparing the intermediate, which have the characteristics of high efficiency, low cost, easily scaling up and good reproducibility.

In a first aspect, the present disclosure provides a compound represented by Formula C, or a stereoisomer thereof:

C

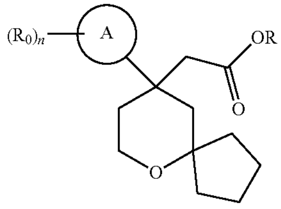

wherein:

R is $C_{1-8}$ alkyl (preferably $C_{1-4}$ alkyl), -$C_{1-4}$alkyl-$C_{6-10}$ aryl (preferably, —$CH_2$-aryl, more preferably, benzyl), or $C_{6-10}$ aryl (preferably, phenyl);

the ring A is a $C_{6-10}$ aromatic ring (preferably, a benzene ring) or five- or six-membered monocyclic heteroaryl ring (preferably, a pyridine ring);

$(R_0)_n$ represents that hydrogen on the ring A is substituted by n $R_0$ groups, where n is 0, 1, 2, 3, or 4; then $R_0$ groups are identical or different and are each independently hydrogen, cyano, acetyl, hydroxyl, hydroxymethyl, hydroxyethyl, carboxyl, halogenated $C_{1-8}$ alkyl (preferably, halogenated $C_{1-4}$ alkyl), halogen (preferably, F or Cl), nitro, $C_{6-10}$ aryl (preferably, phenyl), five- or six-membered monocyclic heteroaryl, $C_{1-8}$ alkyl (preferably, $C_{1-4}$ alkyl), $C_{1-8}$ alkoxyl (preferably, $C_{1-4}$ alkoxyl), $C_{3-6}$ cycloalkyl, $C_{3-6}$ cycloalkoxyl, $C_{2-4}$ alkenyl, $C_{2-4}$ alkynyl, $NR_{11}R_{12}$, —$CONR_{11}R_{12}$, —C(O)O$C_{1-8}$ alkyl (preferably, —C(O)O$C_{1-4}$ alkyl), —OC(O)$C_{1-8}$ alkyl (preferably, —OC(O)$C_{1-4}$ alkyl), —$SO_2C_{1-8}$ alkyl (preferably, —$SO_2C_{1-4}$ alkyl), —$SO_2C_{6-10}$ aryl (preferably, —$SO_2C_6$ aryl, for example, —$SO_2$-phenyl), —$COC_{6-10}$ aryl (preferably, —$COC_6$ aryl, for example, —CO-phenyl), a four- to six-membered saturated monoheterocyclic ring, or a three- to six-membered saturated monocyclic ring, wherein the $C_{6-10}$ aryl, the five- or six-membered monocyclic heteroaryl, the four- to six-membered saturated monoheterocyclic ring, and the three- to six-membered saturated monocyclic ring are each unsubstituted or substituted by one, two, or three substituents selected from the group consisting of acetyl, hydroxyl, cyano, halogen, $C_{1-3}$ alkyl, $C_{1-3}$ alkoxyl, $C_{3-6}$ cycloalkyl, and $NR_{11}R_{12}$; and $R_{11}$ and $R_{12}$ are each independently hydrogen, $C_{1-8}$ alkyl (preferably, $C_{1-4}$ alkyl), halogenated $C_{1-8}$ alkyl (preferably, halogenated $C_{1-4}$ alkyl), $C_{3-6}$ cycloalkyl, or a four- to six-membered saturated monoheterocyclic ring; or $R_{11}$ and $R_{12}$ together with the nitrogen atom linked thereto form a four- to six-membered saturated monoheterocyclic ring, wherein the four- to six-membered saturated monoheterocyclic ring is unsubstituted or substituted with one, two, or three $C_{1-4}$ alkyl groups.

In some embodiments, R is methyl, ethyl, n-propyl, isopropyl, n-butyl, isobutyl or tert-butyl, phenyl, or benzyl, and preferably, methyl.

In some embodiments, A is a phenyl ring, a pyridine ring, a pyrimidine ring, or a triazine ring.

In some embodiments, n is 0.

In some embodiments, the compound represented by Formula C is a compound represented by Formula C2:

C2

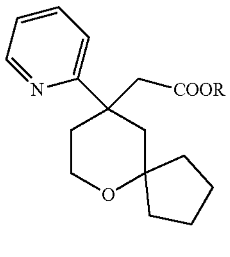

wherein R is methyl, ethyl, n-propyl, isopropyl, n-butyl, isobutyl or tert-butyl, phenyl, or benzyl (preferably, methyl)

In some embodiments, the compound represented by Formula C is a compound represented by Formula C3:

C3

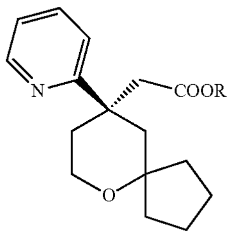

wherein R is methyl, ethyl, n-propyl, isopropyl, n-butyl, isobutyl, tert-butyl, phenyl, or benzyl (preferably, methyl).

A second aspect of the present disclosure provides a preparation method of the compound represented by Formula C or the stereoisomer thereof according to the first aspect. The method includes the following step S200 of:

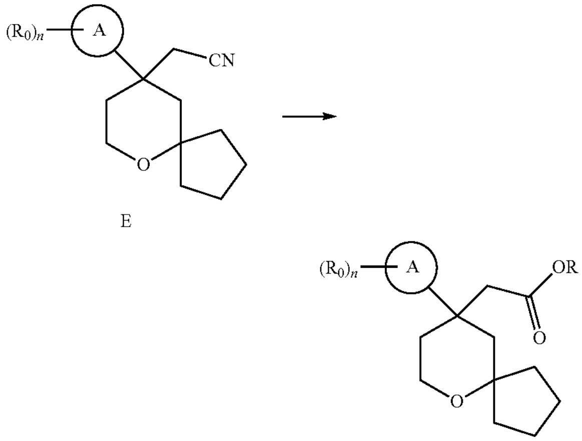

E

C reacting a compound represented by Formula E or a stereoisomer thereof in one or two or more steps to obtain the compound represented by Formula C or the stereoisomer thereof. Further, in step S200, performing an alcoholysis reaction on the compound represented by Formula E or the stereoisomer thereof to obtain the compound represented by Formula C or the stereoisomer thereof.

In some embodiments, in step S200, the compound represented by Formula E or the stereoisomer thereof is subjected to a one-step reaction to obtain the compound represented by Formula C or the stereoisomer thereof.

Specifically, step S200 comprises the steps S211 of: reacting the compound represented by Formula E or the stereoisomer thereof with alcohol (ROH) under the catalysis of an acid; and after the reaction is completed, performing separation and purification to obtain the compound represented by Formula C or the stereoisomer thereof.

In some embodiments, in step S211, the alcohol (ROH) is methanol, ethanol, n-propanol, isopropanol, n-butanol, isobutanol, tert-butanol, phenol, or benzyl alcohol. Further, the alcohol is methanol or ethanol.

In some embodiments, in step S211, the acid is an inorganic acid or an organic acid. Further, the acid is hydrochloric acid or p-toluenesulfonic acid.

In some embodiments, in step S211, said separation and purification includes the following step of: adding water to the reaction liquid after the completion of the reaction to obtain a mixture, adding an organic solvent to the mixture to perform extraction and spin-drying the same to obtain the compound represented by Formula C or the stereoisomer thereof. Further, the organic solvent is methyl tertiary butyl ether.

In some embodiments, in step S200, the compound represented by Formula E or the stereoisomer thereof is subjected to a two-step reaction to obtain the compound represented by Formula C or the stereoisomer thereof:

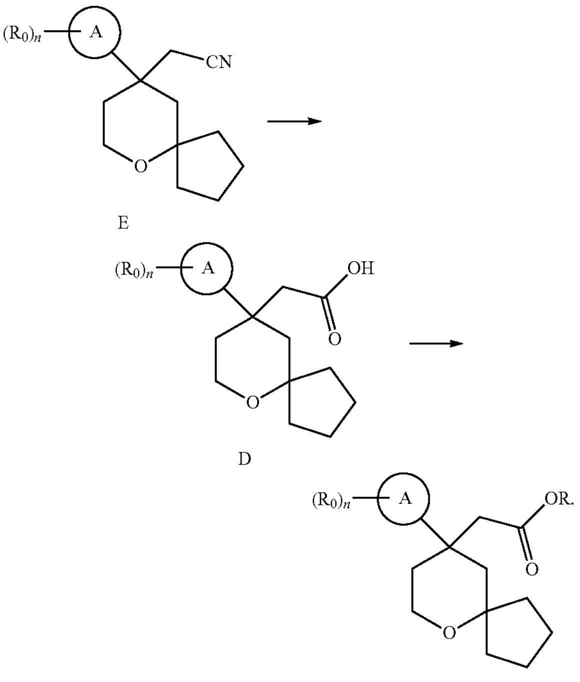

E

D

C

Specifically, step S200 includes the following steps: S221, reacting the compound represented by Formula E or the stereoisomer thereof to obtain a compound represented by Formula D or a stereoisomer thereof; and S222, reacting the compound represented by Formula D or the stereoisomer thereof with ROH to obtain the compound represented by Formula C or the stereoisomer thereof.

In some embodiments, step S221 includes the steps of: mixing the compound represented by Formula E or the stereoisomer thereof with water and an acid, reacting at a temperature of 30° C. to 60° C. (preferably, 45° C. to 50° C.), and performing separation and purification after the reaction is completed to obtain the compound represented by Formula D or the stereoisomer thereof.

In some embodiments, in step S221, the acid is an inorganic acid. Further, the acid is sulfuric acid.

In some embodiments, in step S221, a concentration of the acid in step S221 ranges from 30 g/mL to 60 g/mL.

In some embodiments, in step S221, the compound represented by Formula E or the stereoisomer thereof is mixed with water, the temperature is decreased to 10° C. to 15° C., and sulfuric acid is slowly added dropwise. After the addition is completed, the reaction is carried out (preferably, for 40 min to 80 min) at a temperature of 30° C. to 60° C. (preferably, 45° C. to 50° C.). After the reaction is completed, the temperature is decreased to 5° C. to 10° C. An organic solvent (preferably, toluene) and a base solution (preferably, sodium hydroxide or potassium hydroxide solution with mass percentage of 10% to 30%) are added, and stirring is performed for a predetermined time (preferably, 40 min to 80 min). Subsequent to performing the standing, extracting, washing and drying, the compound represented by Formula D or the stereoisomer thereof is obtained.

In some embodiments, step S222 includes the steps of: reacting the compound represented by Formula D or the stereoisomer thereof with an alcohol (e.g., methanol, ethanol) under catalyzed reaction with acid (e.g., thionyl chloride), reacting completely, performing aftertreatment and drying to obtain the compound represented by Formula C or the stereoisomer thereof.

In some embodiments, the stereoisomer of the compound represented by Formula C is a compound represented by Formula C1, and the stereoisomer of the compound represented by Formula E is a compound represented by Formula E1. The reaction route is shown as below:

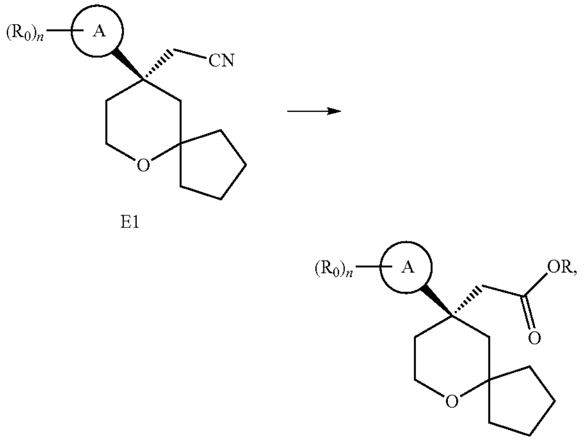

E1

C1 a compound represented by Formula C1 is obtained by reacting the compound represented by Formula E1 in one or more steps.

In some embodiments, the compound represented by Formula C is a compound represented by Formula C2, and the compound represented by Formula E is a compound represented by Formula E2. The reaction route is shown as below:

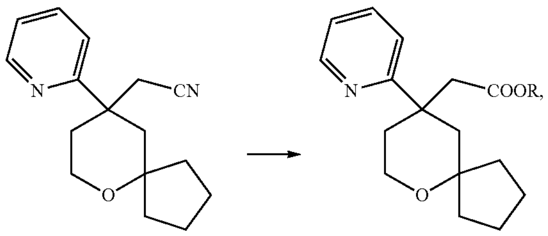

E2 C2 a stereoisomer of a compound represented by Formula C2 is obtained by reacting a compound represented by Formula E2 or a stereoisomer thereof in one or more steps.

In some embodiments, the stereoisomer of the compound represented by Formula C is a compound represented by Formula C3, and the stereoisomer of the compound represented by Formula E is a compound represented by Formula E3. The reaction route is shown as below:

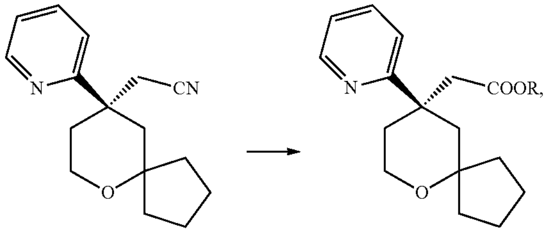

E3 C3 a compound represented by Formula C3 is obtained by reacting the compound represented by Formula E3 in one or more steps.

In the preparation method of the second aspect of the present disclosure, the compound represented by Formula E or the stereoisomer thereof is used as a starting material to produce the compound represented by Formula C or the stereoisomer thereof through a reasonable reaction route. Thus, the preparation method is simple in operations and post-treatment. A product with a higher purity can be obtained simply through a simple purification treatment. A target purity can be obtained without column separation and the like. Therefore, the production difficulty can be greatly reduced, the production cost can be reduced, and the industrial production can be facilitated.

A third aspect of the present disclosure provides a compound represented by Formula B or a stereoisomer thereof:

B

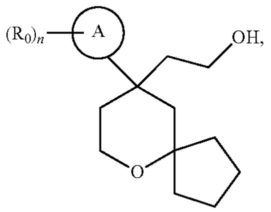

wherein the ring A and $(R_0)_n$ are as defined in the first aspect.

In some embodiments, the compound represented by Formula B is a compound represented by Formula B2:

B2

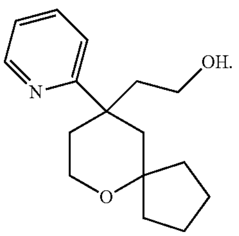

In some embodiments, the compound represented by Formula B is a compound represented by Formula B3:

B3

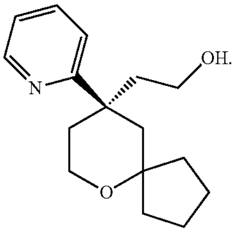

A fourth aspect of the present disclosure provides a preparation method of the compound represented by Formula B or the stereoisomer thereof according to the third aspect. The method includes the following step S400 of:

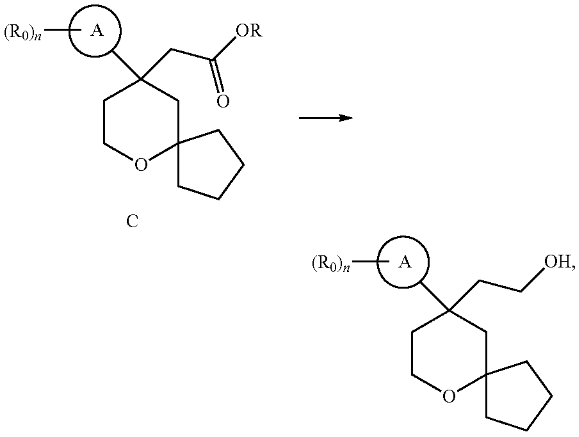

C

B reacting a compound represented by Formula C or a stereoisomer thereof to obtain the compound represented by Formula B or the stereoisomer thereof.

In some embodiments, a reduction reaction is performed in step S400. Further, in step S400, a reduction reaction is performed by using vitride.

In some embodiments, step S400 includes step S410 of mixing the compound represented by Formula C or the stereoisomer thereof with toluene, cooling the mixture to 0° C. to 10° C., slowly adding vitride, then reacting and aftertreating to obtain the compound represented by Formula B or the stereoisomer thereof.

In some embodiments, after the compound represented by Formula B is prepared, step S410 further includes a step of performing chiral resolution to obtain a compound represented by Formula B1.

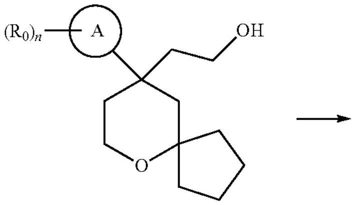

B

-continued

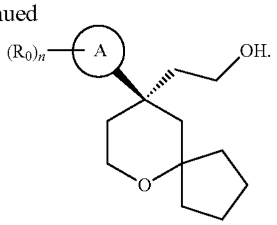

B1

In some embodiments, the chiral resolution may be an instrumental resolution or a chemical resolution.

In some embodiments, the resolving agent for chiral resolution is D-tartaric acid, D-dibenzoyltartaric acid, D-malic acid, D-mandelic acid, D-camphorsulfonic acid, or (R)-(−)-1,1'-binaphthyl-2,2'-diyl hydrogenphosphate. The preferred resolving agent is (R)-(−)-1,1'-binaphthyl-2,2'-diyl hydrogenphosphate.

In some embodiments, the chemical resolution includes the steps of: mixing the compound represented by Formula B with a resolving agent and a first solvent to perform a reaction; after the reaction is completed, removing the first solvent, slurrying with a second solvent, filtering and drying to obtain a solid; dissolving the solid in the first solvent, treating the same at reflux for a predetermined time (preferably, 40 min to 80 min, more preferably, 50 min to 70 min), cooling to precipitate a solid, filtering, and drying to obtain the compound represented by Formula B1. Further, the first solvent is tetrahydrofuran. Further, the second solvent is ethyl acetate. Further, the molar ratio between the compound represented by Formula B and the resolving agent is 1:0.9 to 1:1.1.

By using the racemate compound represented by Formula E as a starting material, a compound represented by Formula C can be obtained through a simple reaction. A reduction reaction is performed to obtain the compound represented by Formula B, and then a chiral resolution is performed. The difficulty of the chiral resolution can be reduced, thereby improving the production efficiency and reducing the production cost.

In some embodiments, in step S410, the compound represented by Formula C1 is reacted to obtain a compound represented by Formula B1:

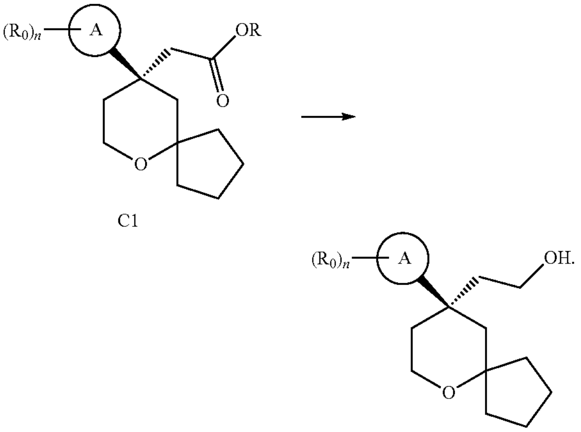

C1

B1

In some embodiments, step S400 is further preceded by a step of preparing the compound represented by Formula C or the stereoisomer thereof by using the preparation method of the second aspect.

A fifth aspect of the present disclosure provides another preparation method of the compound represented by Formula B or the stereoisomer thereof according to the third aspect. The method includes the following step S500 of:

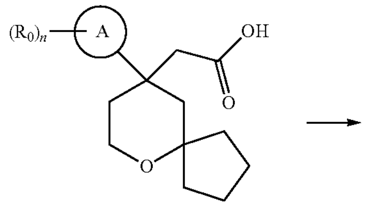

D

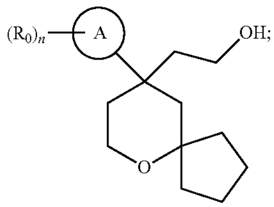

B reacting a compound represented by Formula D or a stereoisomer thereof to obtain a compound represented by Formula B or a stereoisomer thereof.

In some embodiments, a reduction reaction is performed in step S500. Further, in step S500, a reduction reaction is performed by using vitride.

In some embodiments, the stereoisomer of the compound represented by Formula D is represented by Formula D2, and the stereoisomer of the compound represented by Formula B is represented by Formula B3, according to the following reaction route:

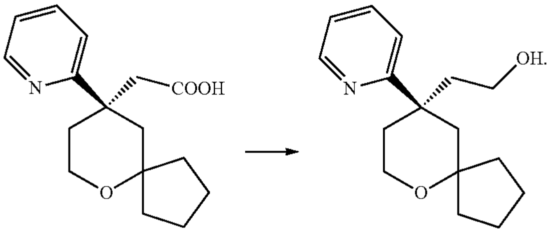

D2 B3

Further, step S500 includes the following step S510 of mixing the compound represented by Formula D or the stereoisomer thereof with toluene, cooling to 0° C.-10° C., adding vitride, and warming to 20° C. to 45° C. to react; after the reaction is completed, quenching the reaction and performing aftertreatment to obtain the compound represented by Formula B or the stereoisomer thereof.

In some embodiments, after the compound represented by Formula B is prepared, step S510 further includes a step of performing chiral resolution to obtain a compound represented by Formula B1:

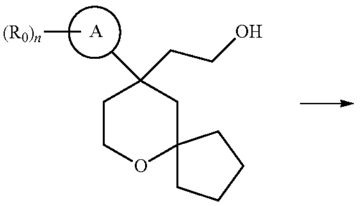

B

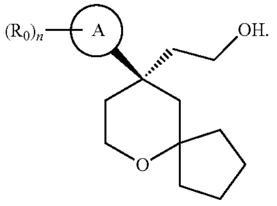

B1

In some embodiments, the chiral resolution may be an instrumental resolution or a chemical resolution.

In some embodiments, the resolving agent for chiral resolution is D-tartaric acid, D-dibenzoyltartaric acid, D-malic acid, D-mandelic acid, D-camphorsulfonic acid, or (R)-(−)-1,1'-binaphthyl-2,2'-diyl hydrogenphosphate. The preferred resolving agent is (R)-(−)-1,1'-binaphthyl-2,2'-diyl hydrogenphosphate.

In some embodiments, the chemical resolution includes the steps of: mixing a compound represented by Formula B with a resolving agent and a first solvent to perform a reaction; after the reaction is completed, removing the first solvent, slurrying with a second solvent, filtering and drying to obtain a solid; dissolving the solid in the first solvent, treating the same at reflux for a predetermined time (preferably, 40 min to 80 min, more preferably, 50 min to 70 min), cooling to precipitate a solid, filtering, and drying to obtain a compound represented by Formula B1. Further, the first solvent is tetrahydrofuran. Still further, the second solvent is ethyl acetate. Further, the molar ratio between the compound represented by Formula B and the resolving agent is 1:0.9 to 1:1.1.

By using the racemate compound represented by Formula D as a starting material, a compound represented by Formula B can be obtained by the reduction reaction, and then, the chiral resolution is performed. The difficulty of the chiral resolution can be reduced, thereby improving the production efficiency and reducing the production cost. In some embodiments, prior to step S500, a step of preparing the compound represented by Formula D or the stereoisomer thereof is performed. Particularly, the step of preparing the compound represented by Formula D or the stereoisomer thereof includes the following step S520 of:

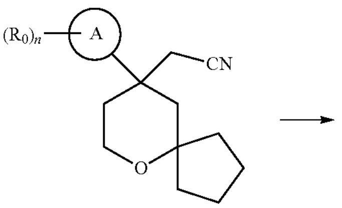

E

-continued

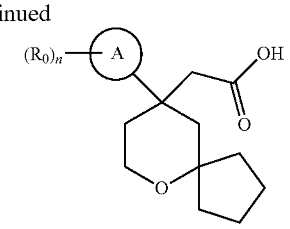

D mixing the compound represented by Formula E or the stereoisomer thereof with water and an acid, reacting at a temperature of 30° C. to 60° C. (preferably, 45° C. to 50° C.), and performing separation and purification after the reaction is completed to obtain the compound represented by Formula D or the stereoisomer thereof.

In some embodiments, in step S520, the acid is an inorganic acid. Still further, the acid is sulfuric acid. Still further, the concentration of the acid is 30 g/mL to 60 g/mL.

In some embodiments, in step S520, the compound represented by Formula E or the stereoisomer thereof is mixed with water, the temperature is decreased to 10° C. to 15° C., and sulfuric acid is slowly added dropwise. After the addition is completed, the reaction is carried out (preferably, for 40 min to 80 min) at a temperature of 30° C. to 60° C. (preferably, 45° C. to 50° C.). After the reaction is completed, the temperature is decreased to 5° C. to 10° C. An organic solvent (preferably, toluene) and a base solution (preferably, sodium hydroxide or potassium hydroxide solution with mass percentage of 10% to 30%) are added, and stirring is performed for a predetermined time (preferably, 40 min to 80 min). Subsequent to performing the standing, extracting, washing and drying, the compound represented by Formula D or the stereoisomer thereof is obtained.

In some embodiments, a stereoisomer of a compound represented by Formula E is represented by Formula E3, and a stereoisomer of a compound represented by Formula D is represented by Formula D2. The reaction route is as below:

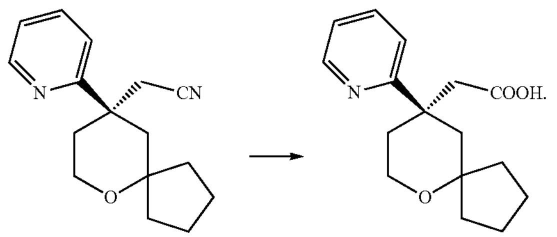

E3 D2

In a sixth aspect, the present disclosure provides a compound having the structure represented by Formula X or Formula Y:

X

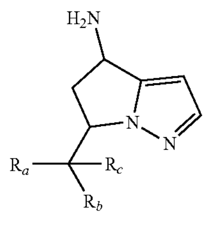

-continued

Y

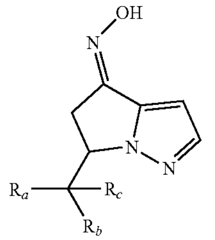

$R_a$ and $R_b$ are each independently hydrogen, halogen (preferably, F or Cl), $C_{1-6}$ alkyl (preferably, $C_{1-3}$ alkyl), halogenated $C_{1-6}$ alkyl (preferably, halogenated $C_{1-3}$ alkyl), or halogenated $C_{1-6}$ alkoxyl (preferably, halogenated $C_{1-3}$ alkoxyl); or $R_a$ and $R_b$ together with the carbon atom linked thereto form a four- to six-membered saturated monoheterocyclic ring or a three- to six-membered saturated monocyclic ring, wherein the four- to six-membered saturated monoheterocyclic ring and the three- to six-membered saturated monocyclic ring are each unsubstituted or substituted by one, two, or three substituents selected from the group consisting of cyano, hydroxyl, hydroxymethyl, cyanomethyl, halogen, $C_{1-3}$ alkoxyl, $C_{1-3}$ alkyl, —$COC_{1-3}$ alkyl, —$CONR_{a1}R_{b1}$, $NR_{a1}R_{b1}$, —$NHCOC_{1-3}$ alkyl, —$NHCONR_{a1}R_{b1}$, —$NHSO_2C_{1-3}$ alkyl, —$NHSO_2NR_{a1}R_{b1}$, and —$NHSO_2C_{3-6}$ cycloalkyl;

$R_c$ is hydrogen, halogen (preferably, F or Cl), $C_{1-6}$ alkyl (preferably, $C_{1-3}$ alkyl), $C_{2-6}$ alkenyl (preferably, $C_{2-4}$ alkenyl), $C_{2-6}$ alkynyl (preferably $C_{2-4}$ alkynyl), $C_{1-6}$ alkoxyl (preferably, $C_{1-3}$ alkoxyl), halogenated $C_{1-6}$ alkyl (preferably, halogenated $C_{1-3}$ alkyl), halogenated $C_{1-6}$ alkoxyl (preferably, halogenated $C_{1-3}$ alkoxyl), —$COC_{1-6}$ alkyl (preferably, —$COC_{1-3}$ alkyl), —$CONR_{a1}R_{b1}$, $NR_{a1}R_{b1}$, —$NHCOC_{1-6}$ alkyl (preferably, —$NHCOC_{1-3}$ alkyl), —$NHCONR_{a1}R_{b1}$, —$NHSO_2C_{1-3}$ alkyl, —$NHSO_2NR_{a1}R_{b1}$, —$NHSO_2C_{3-6}$ cycloalkyl, —$SO_2C_{1-3}$ alkyl, —$SO_2NR_{a1}R_{b1}$, a four- to six-membered saturated monoheterocyclic ring, $C_{6-10}$ aryl, or five- or six-membered monocyclic heteroaryl, wherein the four- to six-membered saturated monoheterocyclic ring, the $C_{6-10}$ aryl, and the five- or six-membered monocyclic heteroaryl are each unsubstituted or substituted by one, two, or three substituents selected from the group consisting of cyano, hydroxyl, hydroxymethyl, cyanomethyl, halogen, $C_{1-3}$ alkoxyl, $C_{1-3}$ alkyl, —$COC_{1-3}$ alkyl, —$CONR_{a1}R_{b1}$, $NR_{a1}R_{b1}$, —$NHCOC_{1-3}$ alkyl, —$NHCONR_{a1}R_{b1}$, —$NHSO_2C_{1-3}$ alkyl, —$NHSO_2NR_{a1}R_{b1}$, and —$NHSO_2C_{3-6}$ cycloalkyl;

$R_{a1}$ and $R_{b1}$ are each independently hydrogen, $C_{1-6}$ alkyl (preferably, $C_{1-3}$ alkyl), halogenated $C_{1-6}$ alkyl (preferably, halogenated $C_{1-3}$ alkyl), $C_{3-6}$ cycloalkyl or a four- to six-membered saturated monoheterocyclic ring; or $R_{a1}$ and $R_{b1}$ together with the nitrogen atom linked thereto form a four- to six-membered saturated monoheterocyclic ring, wherein the four- to six-membered saturated monoheterocyclic ring is unsubstituted or substituted with one, two, or three $C_{1-3}$ alkyl groups.

In an embodiment, $R_a$ and $R_b$ are each independently hydrogen, fluoro or methyl; or $R_a$ and $R_b$ together with the carbon atom linked thereto form cyclopropyl, cyclobutyl or cyclopentyl ring; and $R_c$ is hydrogen, fluoro, methyl, ethyl, methoxy, or trifluoromethyl.

In an embodiment, $R_a$ and $R_b$ are each independently hydrogen, fluoro, or methyl; and $R_c$ is hydrogen, fluoro, methyl, ethyl, methoxy, or trifluoromethyl.

In an embodiment, $R_a$ is methyl, $R_b$ is H, and $R_c$ is methyl.

In an embodiment, the compound represented by Formula X is a compound represented by Formula X-1, and the compound represented by Formula Y is a compound represented by Formula Y-1:

X

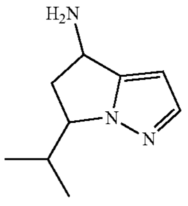

Y-1

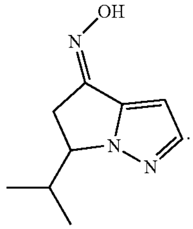

In an embodiment, the compound represented by Formula X is a compound represented by Formula X1:

X1

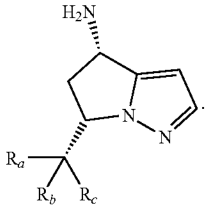

A seventh aspect of the present disclosure provides a preparation method of the compound represented by Formula X or the stereoisomer thereof according to the sixth aspect. The method includes the following steps:

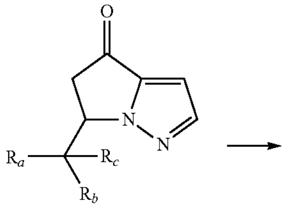

Z

-continued

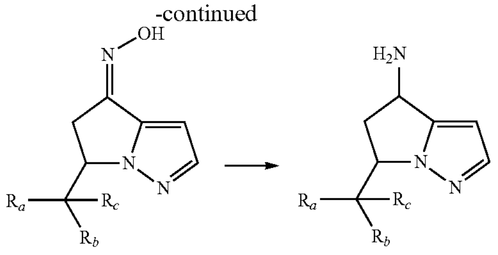

Y X

S710, reacting a compound represented by Formula Z or a stereoisomer thereof to obtain a compound represented by Formula Y or a stereoisomer thereof; and S720, reacting the compound represented by Formula Y or the stereoisomer thereof to obtain the compound represented by Formula X or the stereoisomer thereof.

In some embodiments, step S710 includes the step of mixing the compound represented by Formula Z with hydroxylamine hydrochloride, a base (preferably, pyridine), and an alcohol solvent (preferably, anhydrous methanol), and reacting at a temperature of 50° C. to 70° C. (preferably, 65° C.), to obtain the compound represented by Formula Y.

In some embodiments, a molar ratio of the compound represented by Formula Z to hydroxylamine hydrochloride is 1:1.1 to 1:1.5. Further, a molar ratio of the compound represented by Formula Z to the base is 1:1.1 to 1:1.5. Further, a molar ratio of the compound represented by Formula Z to the base is 1:1.2.

In some embodiments, a compound represented by Formula X or a stereoisomer thereof is prepared by reduction in step S720. Further, step S720 includes the steps of mixing the compound represented by Formula Y or the stereoisomer thereof with a solvent (preferably, anhydrous methanol), adding Pd/C and carrying out the reaction under an atmosphere of hydrogen at a pressure of 15 atm to 20 atm, preferably at 50° C. to 75° C.; and after completion of the reaction (preferably 1 h to 3 h), obtaining the compound represented by Formula X or the stereoisomer thereof.

In some embodiments, in step S720, the stereoisomer of the compound represented by Formula X is a compound represented by Formula X1. The compound represented by Formula X1 is prepared by the step of performing a chiral resolution on a compound represented by Formula X to obtain a compound represented by Formula X1:

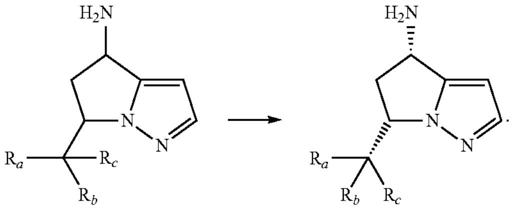

X X1

In some embodiments, the chiral resolution may be an instrumental resolution or a chemical resolution.

In some embodiments, the resolution is performed by a chemical resolution method. Further, the resolving agent is L-tartaric acid, L-dibenzoyl tartaric acid, L-malic acid, L-mandelic acid, L-camphorsulfonic acid, or (S)-(+)-1,1'-Binaphthyl-2,2'-diyl hydrogenphosphate, and preferably L-tartaric acid.

In some embodiments, the above method of chemical resolution includes the steps of: mixing a compound represented by Formula X with a solvent (preferably, ethanol) to obtain a first solution, and mixing a resolving agent (preferably, L-tartaric acid) with a solvent (preferably, ethanol) to obtain a second solution; slowly adding the second solution to the first solution, with precipitating a large amount of solid, filtering, washing and drying the solid to obtain a crude product of a salt of the compound represented by Formula X1; further, subjecting the obtained crude product of the salt of the compound represented by Formula X1 to a refining step.

In some embodiments, subsequent to obtaining the crude product of the salt of the compound represented by Formula XI, the following steps are performed:

S721, repeatedly performing recrystallization treatment on the crude product of the salt of the compound represented by Formula X1 to obtain a refined salt of the compound represented by Formula X1;

S722, dissolving the refined salt of the compound represented by Formula X1 in water and adjusting the pH to 10.5 to 11.5, and extracting the solution to obtain a stereoisomer of the compound represented by Formula X1; and S723: dissolving the refined salt of the compound represented by Formula XI in water, filtering to remove insolubles, collecting the filtrate, adding methanol to the filtrate, and allowing to stand overnight until crystals precipitate to obtain a single crystal of the salt of the compound represented by Formula XI.

In some embodiments, in step S721, two recrystallization treatments are performed. The crude product of the salt of the compound represented by Formula X1 is subjected to a first recrystallization treatment, and the collected crystals are subjected to a second recrystallization treatment.

The first recrystallization treatment step includes: adding the crude product of the salt of the compound represented by Formula X1 into an alcohol-water solvent (preferably, a mixed solvent consisting of methanol and water in a volume ratio of 1:0.8 to 1:1.2), and increasing the temperature to an internal temperature of 65 to 70° C., until the system is clear; slowly adding an alcohol solvent (preferably, methanol) dropwise into the system, controlling the internal temperature to be not less than 55° C., reducing the internal temperature to 46 to 47° C., and continuing stirring for 30 to 90 min; gradually reducing the temperature to room temperature and stirring to precipitate a solid, and collecting the solid to obtain a primary fine product.

The second recrystallization treatment step includes: dissolving the primarily refined product obtained from the first recrystallization treatment in water, then adding an alcohol solvent (preferably, anhydrous methanol), and heating for reflux dissolution; lowering the internal temperature to about 40° C. to 55° C. (preferably, 50° C.), stirring for 30 to 90 min, gradually lowering to room temperature, stirring with a solid precipitated, collecting and washing the solid (preferably, with isopropanol) to obtain a refined salt of a compound represented by Formula X1.

In some embodiments, in the step of the first recrystallization treatment, 2 to 5 mL alcohol-water solvent is added per 1 g of the crude product of the salt of the compound represented by Formula X1, and 8 to 12 mL alcohol solvent is added after warming to an internal temperature of 65° C. to 70° C.

In some embodiments, in the second recrystallization treatment, 1 to 3 mL water, 7 to 1 mL alcohol solvent are added per 1 g of primary competitive product.

In some embodiments, in step S722, 4 to 6 mL water is added per 1 g of the refined salt of the compound represented by Formula XI.

In some embodiments, in step S723, 0.2 to 0.5 mL water and 0.2 to 0.5 mL methanol are added per 100 mg of the refined salt of the compound represented by Formula XI.

An eighth aspect of the present disclosure provides a preparation method of the compound represented by Formula I. The method includs the following steps:

S810 of reacting a compound represented by Formula B or a stereoisomer thereof to obtain a compound represented by Formula A or a stereoisomer thereof:

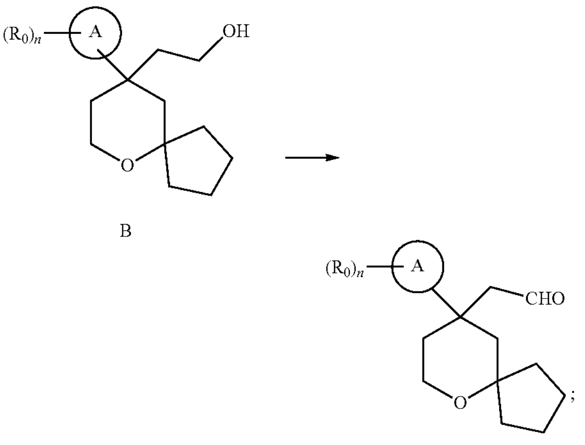

B

A and 820, reacting the compound represented by Formula A or the stereoisomer thereof with a compound represented by Formula X or a stereoisomer thereof to obtain the compound represented by Formula I or the stereoisomer thereof:

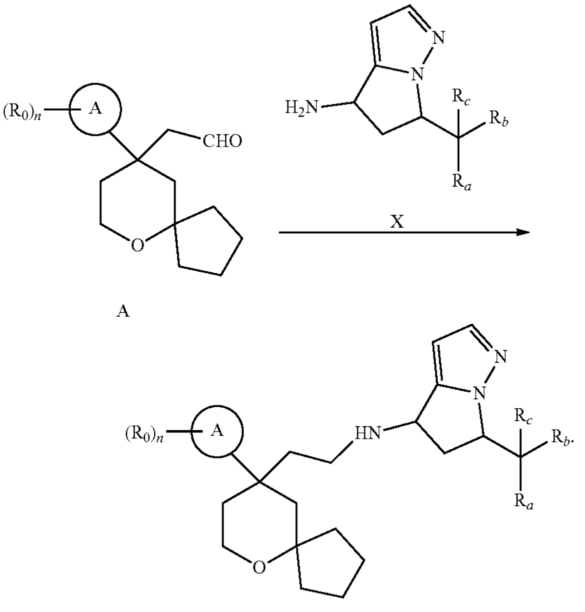

A

I

The ring A and $(R_0)_n$ are as described in the first aspect. $R_a$, $R_b$ and $R_c$ are as described in the sixth aspect.

In some embodiments, in step S810, the compound represented by Formula B is prepared as described in the fourth and fifth aspects.

In some embodiments, in S810, the alcohol hydroxyl is oxidized to aldehyde with 2-iodoxybenzoic acid (IBX). Further, in step S810, a molar ratio of the compound represented by Formula B to IBX is 1:2 to 1:3.

In some embodiments, the compound represented by Formula B is a compound represented by Formula B3, which is oxidized to obtain a compound represented by Formula A1:

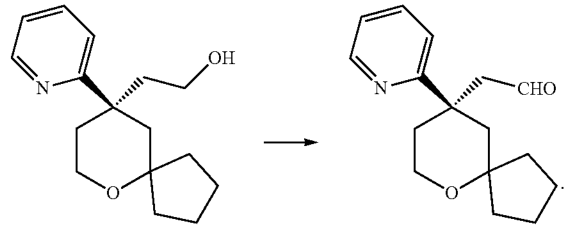

B3 A1

In some embodiments, the compound represented by Formula B3 is prepared by the following method:

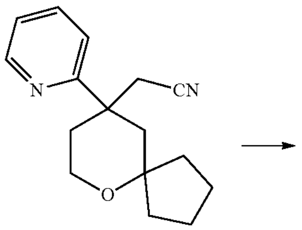

E2

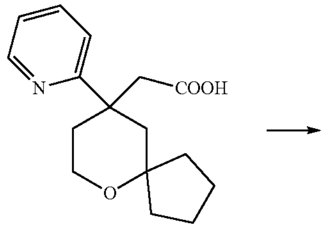

D1

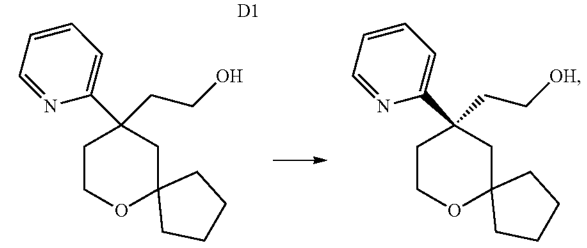

B2 B3

(1) reacting a compound represented by Formula E2 to obtain a compound represented by Formula D1;

(2) reacting the compound represented by Formula D1 to obtain a compound represented by Formula B2; and (3) performing a chiral resolution on the compound represented by Formula B2 to obtain the compound represented by Formula B3.

In some embodiments, the compound represented by Formula B3 is prepared by the following method:

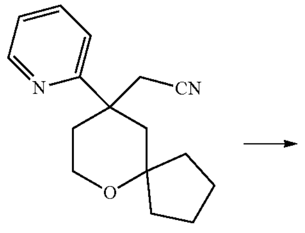

E2

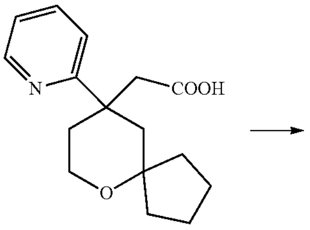

D1

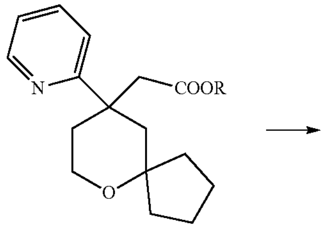

C2

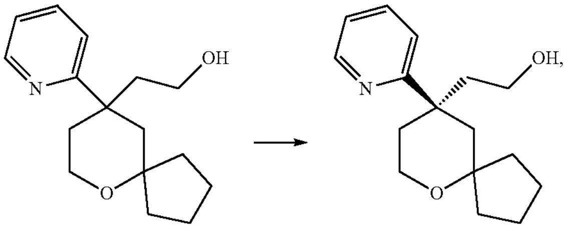

B2 B3

(1) reacting a compound represented by Formula E2 to obtain a compound represented by Formula D1;

(2) reacting the compound represented by Formula D1 to obtain a compound represented by Formula C2;

(3) reacting the compound represented by Formula C2 to obtain a compound represented by Formula B2; where R in the compound represented by Formula C2 is as described in the first aspect; and (4) performing a chiral resolution on the compound represented by Formula B2 to obtain the compound represented by Formula B3.

In some embodiments, the compound represented by Formula B3 is prepared by the following method:

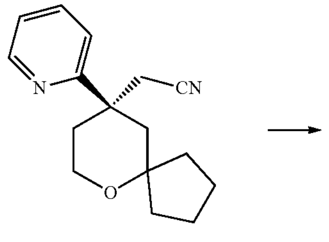

E3

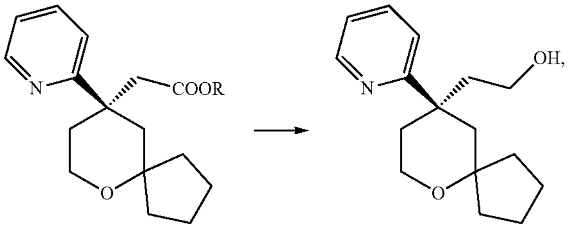

C3 B3

(1) reacting a compound represented by Formula E3 to obtain a compound represented by Formula C3; and (2) reacting the compound represented by Formula C3 to obtain a compound represented by Formula B3.

In some embodiments, the compound represented by Formula B3 is prepared by the following method:

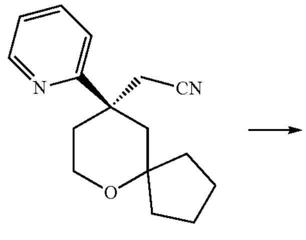

E3

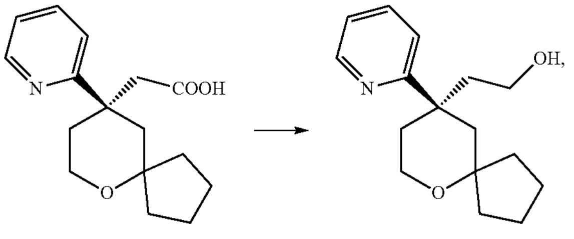

D2 B3

(1) reacting a compound represented by Formula E3 to obtain a compound represented by Formula D2; and (2) reacting the compound represented by Formula D2 to obtain a compound represented by Formula B3.

In some embodiments, in step S820, the compound represented by Formula X or the stereoisomer thereof is prepared as described in the seventh aspect.

In some embodiments, in step S820, a molar ratio of the compound represented by Formula A to the compound represented by Formula X is 1:0.8 to 1:1.2.

In some embodiments, step S820 includes the steps of: mixing a compound represented by Formula A or a stereoisomer thereof with a compound represented by Formula X or a stereoisomer thereof, sodium cyanoborohydride and a solvent, reacting, performing separation and purification to obtain a compound represented by Formula I or a stereoisomer thereof.

In some embodiments, the compound represented by Formula A is a compound represented by Formula A1. The compound represented by Formula X is a compound represented by Formula X1-1. In step 820, the compound represented by Formula A1 is reacted with the compound represented by Formula X1-1 to obtain a compound represented by Formula I-1:

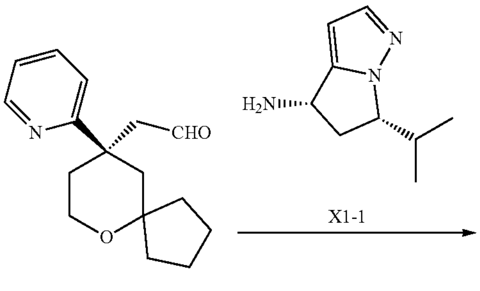

A1 X1-1

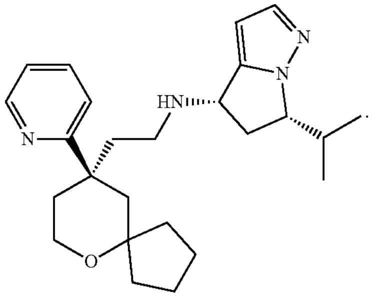

I-1

In some embodiments, the compound represented by Formula X1-1 is selected from a free base of the compound represented by Formula X1-1; or an L-tartrate, L-dibenzoyltartrate, L-malate, L-mandelate, L-camphorsulfonate, or (S)-(+)-1,1'-Binaphthyl-2,2'-diyl hydrogenphosphate thereof, and preferably an L-tartrate thereof.

In the present disclosure, by optimizing the reaction route, novel MOR agonist compounds represented by Formula I with a higher ee value can be obtained in a higher yield. The reaction conditions of the respective steps of the above-mentioned method are milder, the post-treatment is simple and convenient, faciliating the scale-up production is easy. The method has a higher industrial application value.

It should be understood that, without going beyond the scope of the present disclosure, each of the above-described features of the present disclosure and each of the features described in detail below (e.g. in the embodiments) may be combined with each other to form new or preferred technical solutions, which will not be repeated herein due to the limited length of the present disclosure.

BRIEF DESCRIPTION OF THE DRAWINGS

FIG. 1 is a single crystal structure of L-tartrate of a compound X1-1.

DETAILED DESCRIPTION

Definition of Terms

As used herein, "alkyl" refers to both linear and branched chain saturated aliphatic hydrocarbon groups, $C_{1-8}$ alkyl being an alkyl containing 1 to 8 carbon atoms, preferably $C_{1-4}$ alkyl, and more preferably $C_{1-3}$ alkyl, and other are similarly defined. Examples of alkyl include, but not limited to: methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4dimethylhexyl, 2-ethylhexyl, 3-ethylhexyl, 4-ethylhexyl, 2-methyl-2-ethylpentyl, 2-methyl-3-ethylpentyl, and more preferably, various branched chain isomers thereof and the like.

As used herein, "alkenyl" refers to a linear or branched carbon chain containing at least one carbon-carbon double bond. $C_{1-4}$ alkenyl is an alkenyl group containing 1 to 4 carbon atoms. Examples of alkenyl include, but not limited to: vinyl, allyl, isopropenyl, pentenyl, hexenyl, heptenyl, 1-propenyl, or 2-butenyl.

As used herein, "lkynyl" refers to a linear or branched carbon chain containing at least one carbon-carbon triple bond. $C_{1-4}$ alkynyl is an alkynyl containing 1 to 4 carbon atoms. Examples of alkynyls include ethynyl and propargyl.

As used herein, "$C_{6-10}$ aryl" and "$C_{6-10}$ aryl ring", which may be used interchangeably, both refer to an all-carbon monocyclic or fused polycyclic (i.e. rings that share an adjacent pair of carbon atoms) group having a conjugated n-electron system, containing 6 to 10 carbon atoms, preferably, phenyl and naphthyl, and more preferably, phenyl.

As used herein, "five- or six-membered monocyclic heteroaryl ring" and "five- or six-membered monocyclic heteroaryl", which may be used interchangeably, both refer to a single heteroaryl ring containing 5 to 6 ring atoms, for example, including, but not limited to: a thiophene ring, an N-alkane ring pyrrole ring, a furan ring, a thiazole ring, an imidazole ring, an oxazole ring, a pyrrole ring, a pyrazole ring, a triazole ring, a 1,2,3-triazole ring, a 1,2,4-triazole ring, a 1,2,5-triazole ring, a 1,3, 4-triazole ring, a tetrazole ring, an isoxazole ring, an oxadiazole ring, a 1,2,3-oxadiazole ring, a 1,2,4-oxadiazole ring, a 1,2,5-oxadiazole ring, a 1,3,4-oxadiazole ring, a thiadiazole ring, a pyridine ring, a pyridazine ring, a pyrimidine ring, a pyrazine ring, and the like; and preferably, a pyridine ring.

As used herein, "halogenated $C_{1-8}$ alkyl" refers to that alkyl is substituted with one or more (e.g., 1, 2, 3, 4, or 5) halogens, alkyl being defined as above, for example, halogenated $C_{1-4}$ alkyl. Examples of halogenated $C_{1-8}$ alkyl include, but not limited to: monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, and the like.

As used herein, "$C_{1-8}$ alkoxy" refers to —O-($C_{1-8}$ alkyl), alkyl being defined as above, $C_{1-4}$ alkoxyl is preferred, and $C_{1-3}$ alkoxyl is more preferred. Examples include, but not limited to: methoxyl, ethoxyl, propoxyl, isopropoxyl, butoxyl, tert-butoxyl, isobutoxyl, pentyloxyl, and the like.

As used herein, "cycloalkyl" and "cycloalkyl ring" are used interchangeably and both refer to a saturated or partially unsaturated monocyclic cyclic hydrocarbyl. "$C_{3-6}$ cycloalkyl" refers to a cyclic hydrocarbyl containing 3 to 6 carbon atoms. Examples of cycloalkyl include, but not limited to: cyclopropyl, cyclobutyl, cyclopentyl, cyclopentenyl, cyclohexyl, cyclohexenyl, cyclohexadienyl and the like, preferably, cyclopropyl, cyclopentyl, and cyclohexenyl.

As used herein, "$C_{3-6}$ cycloalkoxy" refers to —O-($C_{3-6}$ cycloalkyl), where cycloalkyl is defined as above. Examples include, but not limited to: cyclopropyloxy, cyclobutyloxy, cyclopentyloxy, cyclohexyloxy, and the like.

As used herein, a "three- to six-membered saturated monocyclic ring" refers to a saturated all-carbon monocyclic ring containing 3 to 6 ring atoms. Examples of three- to six-membered saturated monocyclic rings include, but are not limited to: a cyclopropyl ring, a cyclobutyl ring, a cyclopentyl ring, a cyclohexyl ring, and the like.

As used herein, "four- to six-membered saturated monoheterocyclic ring" refers to a four- to six-membered monocyclic ring, in which 1, 2 or 3 carbon atoms are substituted by a heteroatom selected from nitrogen, oxygen or $S(O)_t$, where t is an integer from 0 to 2, but excluding the ring portion of —O—O—, —O—S— or —S—S—, the remaining ring atoms being carbon. The "four- to six-membered saturated monoheterocyclic ring" is preferably five- to six-membered saturated monoheterocyclic ring. Examples of the four- to six-membered saturated monoheterocyclic rings include, but are not limited to: azetidine, oxetane, tetrahydrofuran, tetrahydrothiophene, tetrahydropyrrole, piperidine, oxazolidine, piperazine, dioxolane, dioxane, morpholine, thiomorpholine, thiomorpholine-1,1-dioxide, tetrahydropyran, and the like.

As used herein, "halogen" refers to fluorine, chlorine, bromine, or iodine.

As used herein, "stereoisomers" refers to that the compound of the present disclosure may contain one or more chiral centers and exist in different optically active forms. When the compound of the present disclosure contains one chiral center, each such chiral center will independently produce two optical isomers. Diastereomers may exist when the compound of the present disclosure contains more than one chiral center. The scope of the present disclosure includes all possible optical isomers and diastereomeric mixtures and pure or partially pure compounds.

In the present disclosure, the compound represented by Formula E may be one of commercially available starting material (e.g., CAS NO. 1401031-37-5; CAS NO. 1401031-38-6).

In the present disclosure, the timing of the introduction of the chiral center is not particularly limited, and chiral resolution can be performed after the preparation of the corresponding compound, or the preparation can be performed directly using a starting material having chirality, both of which shall fall within the scope of the present disclosure.

The present disclosure is further described by the following specific examples. It should be understood that these examples are illustrative only and are not intended to limit the scope of the present disclosure. The following examples without indicating the specific experimental procedure shall generally follow conventional conditions or conditions suggested by the manufacturer. Percentages and parts are calculated by weight, unless otherwise indicated. Unless otherwise defined, the terms used herein have the same meaning as is familiar to those skilled in the art. Moreover, any methods and materials similar or equivalent to those described herein can be used in the present disclosure.

As used herein, THF represents tetrahydrofuran, EA represents ethyl acetate, PE represents petroleum ether, DMF represents dimethylformamide, DMSO represents dimethylsulfoxide, r. t. represents room temperature, DCM represents dichloromethane, DBU represents 1,8-diazabicycloundec-7-ene, TEMPO represents 2,2,6,6-tetramethylpiperidine oxide, oxone represents potassium peroxymonosulfonate, IBX represents 2-iodoxybenzoic acid, MeOH is methanol, EtOH represents ethanol, IPA represents isopropanol, and ACN represents acetonitrile.

As used herein, the room temperature refers to a temperature about 20° C. to 25° C.

EXAMPLE 1

Preparation of intermediate X1-1a

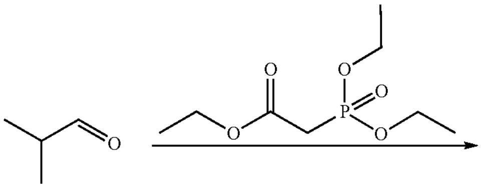

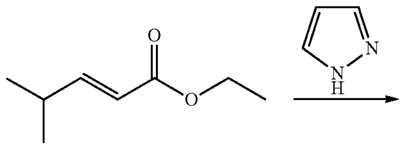

v1

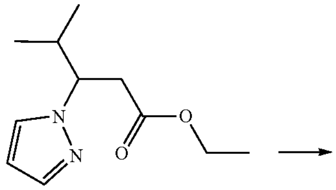

v2

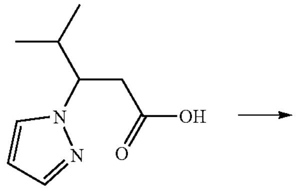

v3

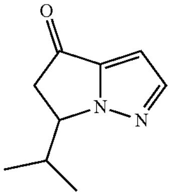

X1-1a

Step 1: triethyl phosphonoacetate (476 mL, 2.4 mol), DBU (365 g, 2.4 mol), lithium chloride (127 g, 3 mol), and acetonitrile (1.2 L) were added to a 3 L single-neck flask and stirred at room temperature under the protection of argon for 20 minutes. The mixture was cooled to 0° C. (internal temperature) and slowly added with isobutyraldehyde (144 g, 2 mol) dropwise, followed by stirring at room temperature for 12 hours. The mixture was then filtered, and the filter cake was washed with EA (100 mL×2). Thereafter, water (1 L) was added, and the mixture was extracted with EA (1.5 L*2), washed with saturated sodium chloride, dried over anhydrous sodium sulfate and spin-dried to obtain a compound v1 (175 g).

Step 2: DMF (1 L) was added to a 3 L single-neck flask loaded with compound v1 (300 g, 2.1 mol); with stirring, potassium carbonate (579 g, 4.2 mol) and pyrazole (287g, 4.2 mol) were added and stirred at 65° C. for 18 hours and spin-dried directly. The remaining solid was slurried with acetonitrile (150 ml) and filtered to obtain a white solid, followed by filtering. The filter cake was washed with EA (500 mL×2), and then washed with the saturated salt solution (300 mL×3), dried over anhydrous sodium sulfate, spin-dried and purified by the column chromatography (PE with 5% EA as a mobile phase), to obtain a compound v2 (258 g). MS m/z (ESI):211.1 $[M+1]^+$.

Step 3: potassium hydroxide (133 g, 3.32 mol) was dissolved by adding water (200 mL), and the mixture was pre-cooled to 5° C. A 3 L flask was added with the compound v2 (465 g, 2.21 mol), methanol (0.5 L), THF (0.5 L), and a pre-cooled aqueous solution of potassium hydroxide, and the mixture was stirred for 2 h. The pH was adjusted to about 3 with concentrated hydrochloric acid. The mixture was extracted with DCM (800 ml×2). All organic phases were combined, washed with saturated brine, dried and concentrated to obtain a compound v3 (410.5 g). MS m/z (ESI):183.1 $[M+1]^+$.

Step 4: the compound v3 (10.2 g, 0.055 mol) and THF (200 mL) was added into a three-neck flask (500 mL) under the protection of nitrogen, and the temperature was reduced to −75° C. 2.5 M THF solution of n-butyllithium (55 mL, 0.137 mol) was added dropwise slowly. After the addition was complete, the temperature was slowly raised to −10° C. and stirring was continued for 3 hours. The reaction was quenched by adding saturated ammonium chloride, added with water (100 mL), and extracted with EA (400 ml×2). The combined organic phase was washed with saturated brine, dried and concentrated to obtain brown liquid. Through purification by column chromatography (mobile phase: PE containg 30% EA), a compound X1-1a (4 g) was obtained. MS m/z (ESI): 165.1 $[M+1]^+$.

EXAMPLE 2

Preparation of Amine X1-1

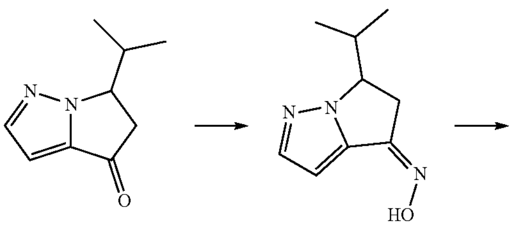

X1-1a X1-1b

-continued

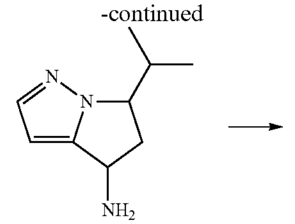

X1-1c

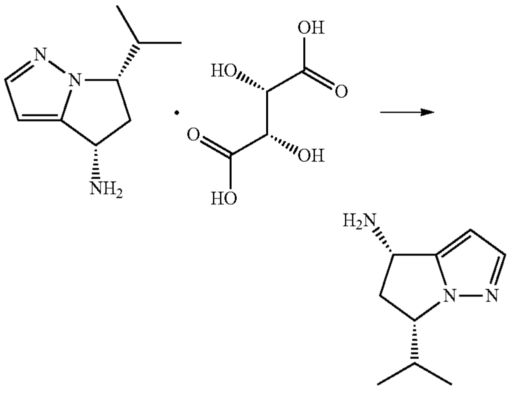

X1-1

Step 1: the compound X1-1a (16.0 g, 97.4 mmol, 1.0 equiv) was added into a 250 mL three-neck flask, and added with anhydrous methanol (128 mL, 8.0 v/w), hydroxylamine hydrochloride (6.85 g, 98.6 mmol, 1.2 equiv), and pyridine (7.80 g, 98.6 mmol, 1.2 equiv). The temperature was raised to 65° C., and the mixture reacted for 1 hour. The reaction liquid was spin-dried, stirred with 160 mL of water, extracted with dichloromethane (80 mL*2), and the organic phases were combined. The organic phase was washed once with 50 mL saturated brine, dried over anhydrous sodium sulfate, filtered and concentrated to obtain a compound X1-1b (16.5 g, $^{1}$HNMR: cis-trans isomer ratio 1:0.4).

Step 2: the compound X1-1b (4.0 g, 22.3 mmol, 1.0 equiv) was dissolved in 80 mL 1 anhydrous methanol, and added with Pd/C (0.4 g). After performing hydrogen replacement three times, an external temperature of the autoclave was maintained at 65° C. and the pressure in the autoclave was maintained at 15 atm to 20 atm. After reacting for 1.5 h, hydrogen absorption was terminated, followed by reacting for 0.5 h. The mixture was filtered and spin-dried to obtain a compound X1-1c. MS m/z (ESI):166.1 $[M+1]^+$.

Step 3: the compound X1-1c (10.1 g, 61.1 mmol, 1.0 equiv) was dissolved in absolute ethanol (20 mL), and the mixture was stirred at room temperature to obtain a solution of compound X1-1c in ethanol. L-Tartaric acid (11.0 g, 73.4 mmol, 1.2 equiv) was dissolved in absolute ethanol (175 mL), and the mixture slowly dropped into the ethanol solution of compound X1-1c, while precipitating a lot of solid. After filtration, the filter cake was washed with a small amount of ethanol and dried to obtain 21.0 g of solid, which was then added into a 500 mL three-neck flask, added with 20 mL water and 20 mL anhydrous methanol. The temperature was increased to an internal temperature of 65° C. to 70° C., until the system is clear. 200 ml of anhydrous methanol was slowly added dropwise in the system to control the internal temperature not less than 55° C. The internal temperature was reduced to 46 to 47° C. and stirring was continued for 1 h. The temperature was reduced to room temperature for about 2 h, and the mixture was stirred overnight. The mixture was filtered, and the filter cake was washed with 20 mL isopropanol. The filter cake was dried to constant weight to obtain 10.3 g of white solid. 10.3 g of the white solid was added with 15 mL of water and 80 mL of anhydrous methanol, and the solution was heated for reflux dissolution. The internal temperature was reduced to about 50° C., and the mixture was stirred for 1 h. The temperature was reduced to room temperature for about 2 h and stirred overnight. The mixture was filtered, and the filter cake was washed with 10 mL isopropanol. The filter cake was dried to constant weight to obtain a L-tartrate salt of the compound X1-1 (5.02 g).

Preparation of L-tartrate salt single crystal of compound X1-1: the L-tartrate salt of compound X1-1 (300 mg) was dissolved in water (1 mL), and the insoluble material was removed by filtration. 1 mL of anhydrous methanol was added dropwise, followed by standing overnight, a small amount of colorless transparent crystals precipitated in the solution. The colorless transparent crystal obtained in this example was subjected to single crystal X-ray analysis by means of Bruker D8 Venture X single crystal diffractometer. The crystal structure diagram of the obtained product is shown in FIG. 1. Thus, the absolute configuration of the compound X1-1 can be deduced from the single crystal structure of the L-tartrate salt of compound X1-1 to be a (4S, 6S) configuration.

Instrument Parameters:

| | |
|---|---|
| Light source: Cu target | X-ray: Cu-Kα (=1.54178 Å) |
| Detector: CMOS Face Detector | Resolution: 0.80 Å |
| Current voltage: 50 kV, 1.2 mA | Exposure time: 50 s |
| Distance of surface detector to sample: 40 mm | Test temperature: 170(2) K |

Step 4: the L-tartrate salt of X1-1 (39 g) was dissolved in water (200 mL), with the pH adjusted to about 11 with saturated aqueous sodium carbonate solution. The mixture was extracted six times with 40 mL dichloromethane, the organic phase was dried over anhydrous sodium sulfate, and the solvent was evaporated under reduced pressure to obtain a compound X1-1 (18.0 g).

EXAMPLE 3-1

Preparation of Racemic Alcohol

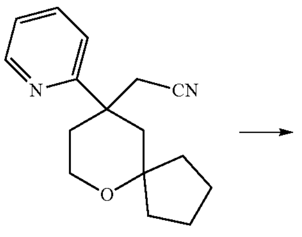

E2

-continued

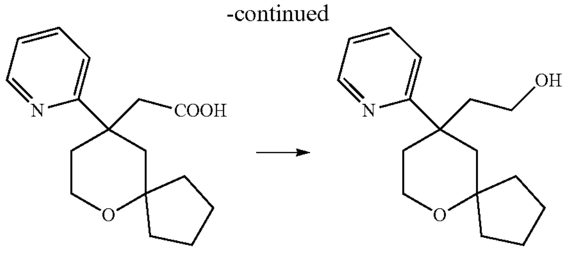

D1 B2

Step 1: compound E2 (20 g, CAS NO. 1401031-37-5) and 80 mL water were added to a 250 mL three-neck flask. The temperature was cooled down to 10 to 15° C. The mixture was stirred, and added with sulfuric acid solution (prepared by adding 11.5 g concentrated sulfuric acid into 20 mL water) dropwise. After the dropwise adding, the mixture was warmed up to 45 to 50° C. The mixture was stirred for 1 hour with the temperature maintained. The temperature was lowered to 5 to 10° C., 100 mL of toluene was added, and 30 g of 20% sodium hydroxide solution was added dropwise. After the dropwise adding, the mixture was stirred at room temperature for 1 hour. The mixture was left to stand for layering, and the organic phase was separated. The aqueous phase was extracted twice with 100 mL of toluene. The combined organic phases were washed once with 100 mL of saturated brine, dried over anhydrous sodium sulfate, filtered. The toluene solution thereof was used for the next step.

Step 2: the above-mentioned toluene solution (containing about 5.1 g of compound D1) was cooled to the temperature of 0 to 10° C. under the protection of nitrogen, and added with 16.9 g of 70% vitride dropwise while maintaining the temperature. After the dropwise adding, the temperature was increased to 40 to 45° C. The mixture was stirred for 1 hour while maintaining the temperature. The temperature was then reduced to 0 to 10° C. 25 mL of water was added dropwise to quench the reaction. 10 mL of 20% sodium hydroxide solution was added, and the mixture was allowed to warm to room temperature and stirred for 1 hour. The mixture was filtered, and the filter cake was rinsed with 100 mL of methyl tertiary butyl ether. The mother liquor was settled for layring to separate the organic phase, and the aqueous phase was extracted again with 50 mL of methyl tertiary butyl ether. The combined organic phases were washed once with 25 mL of saturated brine, dried over anhydrous sodium sulfate, and filtered. The filter cake was rinsed with a small amount of methyl tertiary butyl ether, and the filtrate was concentrated under reduced pressure to obtain compound B2 (4.66 g, yellow oily product, 91.4% yield, 92.6% purity). $^{1}$H NMR(400 MHz, $CDCl_3$): δ 8.55-8.53 (m, 1H), 7.64 (td, $^{3}J$=7.6 Hz, $^{4}J$=2.0 Hz, 1H), 7.32 (d, $^{3}J$=8.0 Hz, 1H), 7.12 (ddd, $^{3}J$=7.6 Hz, $^{3}J$=4.8 Hz, $^{4}J$=1.2 Hz, 1H), 3.74-3.71 (m, 2H), 3.53-3.47 (m, 1H), 3.27-3.21 (m, 1H), 2.43-2.40 (m, 2H), 2.27 (br, 1H), 2.01-1.91 (m, 2H), 1.82-1.72 (m, 3H), 1.67-1.58 (m, 1H), 1.55-1.44 (m, 3H), 1.43-1.33 (m, 1H), 1.12-1.06 (m, 1H), 0.74-0.66 (m, 1H). MS m/z (ESI): 262.1[M+1]$^{+}$.

EXAMPLE 3-2

Preparation of Racemic Alcohol

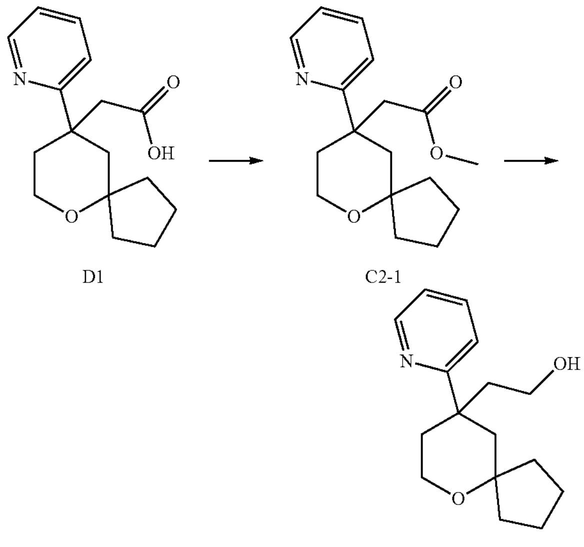

D1 C2-1 B2

Step 1: compound D1 (2.0 g, 7.26 mmol, 1.0 equiv) was dissolved in methanol (10.0 mL, 5.0 v/w), and the mixture was added into a 50 mL three-neck flask. Under the protection of $N_2$ protection and the temperature cooled to 5 to 10° C. $SOCl_2$ (1.08 g, 9.08 mmol, 1.25 equiv) was added dropwise into the three-neck flask for about 10 min, and the internal temperature was controlled at 10 to 15° C. The temperature was raised to 50 to 55° C., and reacted for 3 h. The reaction liquid was spin-dried, and 15 ml of methyl tertiary ether was added. 25% sodium carbonate aqueous solution was added to the system until the pH of the aqueous phase was ajusted to about 9, and the internal temperature was controlled at 10 to 15° C. The liquid was separated, and the aqueous phase was extracted twice with 10 mL of methyl tertiary ether twice.

The combined organic phases were spin-dried to obtain C2-1 (2.0 g, 98.0% purity, 94.7% yield). $^{1}$H NMR(400 MHz, $CDCl_3$): δ 8.57-8.56 (m, 1H), 7.63 (td, $^{3}J$=7.6 Hz, $^{4}J$=1.6 Hz, 1H), 7.32 (d, $^{3}J$=8.0 Hz, 1H), 7.11 (ddd, $^{3}J$=7.6 Hz, $^{3}J$=4.8 Hz, $^{4}J$=0.8 Hz, 1H), 3.79-3.77 (m, 2H), 3.42 (s, 3H), 2.83 (d, $^{2}J$=14.0 Hz, 1H), 2.57-2.43 (m, 3H), 2.00-1.88 (m, 2H), 1.82-1.78 (m, 1H), 1.71-1.61 (m, 1H), 1.57-1.47 (m, 3H), 1.44-1.35 (m, 1H), 1.22-1.16 (m, 1H), 0.82-0.74 (m, 1H). MS m/z (ESI): 290.1[M+1]$^{+}$.

Step 2: compound C2-1 (1.86 g) and 15 mL toluene were added to a 100 mL three-neck flask, and nitrogen displacement was performed for three times. The flask was cooled to an internal temperature of 0 to 10° C., and a vitride solution (6.5 g) was added dropwise. The internal temperature was controlled to be lower than 10° C. About 30 minutes after the addition was completed, the flask was warmed to 40 to 45° C., and the mixture was stirred for 1 h. The reaction liquid was cooled to 0 to 10° C., water (9.3 mL) was added dropwise to quench the reaction, and then 20% NaOH solution (3.7 mL) was added dropwise. After the dropwise adding, the mixture was allowed to warm to room temperature and stirred at 20 to 25° C. for 1 h, followed by filtering. The filter cake was rinsed with methyl tertiary butyl ether (37 mL), and the liquid was separated. The aqueous phase was extracted with methyl tertiary butyl ether (19 mL), followed by separation. The organic phases were combined and washed with saturated NaCl (9.3 mL) and stirred for 15 min. The liquid was separated, and the organic phase was dried with 3.7 g of anhydrous $Na_2SO_4$, concentrated under reduced pressure until no solvent evaporates to obtain compound B2 (1.66 g, purity: 98.49%, yield: 98.8%).

EXAMPLE 3-3

Resolution of Alcohol

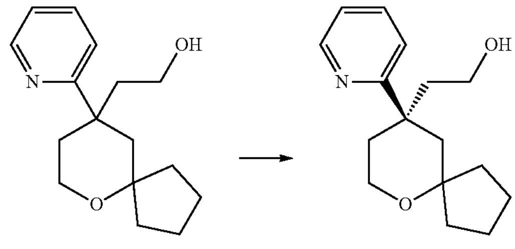

B2 B3

After adding the compound B2 (2.50 g, 9.56 mmol, 1.0 equiv) and (R)-(−)-1,1'-binaphthyl-2,2'-diyl hydrogenphosphate (3.33 g, 9.56 mmol, 1.0 equiv) into 25 mL tetrahydrofuran, the mixture was stirred at room temperature for 1 h. The solvent was evaporated under reduced pressure, added with 20 mL of ethyl acetate to slurry, and the slurry was filtered and dried to obtain a solid (5.0 g). The solid was slurried in 50 mL tetrahydrofuran and refluxed for 1.5 h, cooled to room temperature for further slurrying for 1.5 h. The slurry was filtered and dried to obtain a faint yellow solid (1.83 g, ee %: 84.58%). The resulting solid was further refluxed with 18 mL tetrahydrofuran for 1 h, cooled to room temperature and slurried for 1 h, and filtered. The filter cake was dried to obtain a faint yellow solid (1.03 g, ee %: 91.64%). 1.03 g of filter cake was added into 10 mL tetrahydrofuran for refluxing for 1 h. The mixture was cooled to room temperature and slurried for 1 h, and filtered. The filter cake was dried to obtain a faint yellow solid (0.53 g, ee %: 97.34%). The filter cake was dissolved in 10 mL of water, and pH was adjusted to 9-10 with saturated sodium carbonate solution. The mixture was extracted with dichloromethane (10 mL*3), dried over anhydrous sodium sulfate, filtered and spin-dried to obtain a colorless oily matter (0.23 g, yield 9.1%). $^1$H NMR(400 MHz, $CDCl_3$): δ 8.55-8.54 (m, 1H), 7.65 (td, $^3J$=7.6 Hz, $^4J$=2.0 Hz, 1H), 7.32 (d, $^3J$=8.0 Hz, 1H), 7.12 (ddd, $^3J$=7.6 Hz, $^3J$=4.8 Hz, $^4J$=1.2 Hz, 1H), 3.75-3.72 (m, 2H), 3.54-3.48 (m, 1H), 3.28-3.22 (m, 1H), 2.44-2.40 (m, 2H), 2.03-1.91 (m, 2H), 1.82-1.72 (m, 3H), 1.67-1.59 (m, 1H), 1.55-1.44 (m, 3H), 1.42-1.34 (m, 1H), 1.12-1.06 (m, 1H), 0.74-0.66 (m, 1H). MS m/z (ESI): 262.2[M+1]$^+$. The colourless oily matter obtained and the compound B3 synthesized in Example 4 were analyzed and compared by means of HPLC, and the retention times thereof were identical. In combination with the mass spectral data, it was determined that the colorless oily matter obtained in this example was Compound B3.

EXAMPLE 4

Preparation of Chiral Alcohol

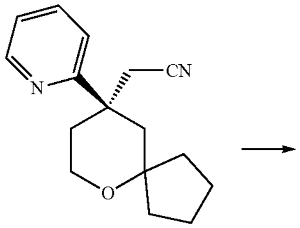

E3

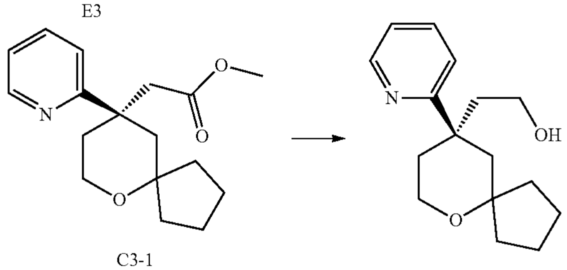

C3-1 B3

Step 1: A 50 mL single-neck flask was added with 1.03 g of the compound E3 (CAS NO. 1401031-38-6), methanol hydrochloride (4 mol/L, 7 mL) and anhydrous methanol (10 mL) under the protection of nitrogen. The mixture was stirred at room temperature for 7 h. Additional methanol hydrochloride (4 mol/L, 3 mL) was added, and the mixture was stirred at room temperature for 2 h. 10 mL of water was added to the above-mentioned reaction. The mixture was stirred at room temperature for 1.0 h. The reaction liquid was concentrated under reduced pressure to dryness, added with 20 mL of methyl tertiary butyl ether and 10 mL of water, and then pH was adjusted to 8 by adding a saturated sodium carbonate solution. The temperature was controlled to be 10 to 30° C. The liquid was separated and the aqueous phase was extracted with 20 mL methyl tertiary butyl ether twice, followed by separation. The organic phases were combined and washed with 20 mL of saturated sodium chloride solution. The organic phase was added with 5 g anhydrous sodium sulfate for drying. After suction filtration, the filter cake was washed with 10 mL of methyl tertiary butyl ether, and the filtrate was concentrated to dryness to obtain compound C3-1 (1.08 g, yield: 93.1%, purity: 99.6%). $^1$H NMR (400 MHz, $CDCl_3$): δ 8.57-8.56 (m, 1H), 7.63 (td, $^3J$=7.6 Hz, $^4J$=1.6 Hz, 1H), 7.32 (d, $^3J$=8.0 Hz, 1H), 7.13-7.10 (m, 1H), 3.79-3.77 (m, 2H), 3.42 (s, 3H), 2.83 (d, $^2J$=14.4 Hz, 1H), 2.57-2.43 (m, 3H), 2.00-1.86 (m, 2H), 1.82-1.75 (m, 1H), 1.69-1.61 (m, 1H), 1.57-1.47 (m, 3H), 1.46-1.34 (m, 1H), 1.22-1.16 (m, 1H), 0.82-0.74 (m, 1H). MS m/z (ESI): 290.1[M+1]$^+$.

Step 2: 0.58 g of the compound C3-1 and 12 mL of toluene were added into a three-neck flask, and the mixture was cooled to 0 to 5° C. 3.0 eq svitride was lowly added dropwise, while the temperature was controlled at 0 to 5° C. After the completion of dropwise addition, the temperature was kept and the mixture was stirred for 0.5 h. The temperature was raised to room temperature (27° C.), and stirred for 1 h while maintaining the temperature. Through after-treatment, compound B3 (0.33 g, yield: 63.2%, purity: 99.33%) was obtained. MS m/z (ESI): 262.2[M+1]$^+$.

EXAMPLE 5

Preparation of Chiral Alcohol

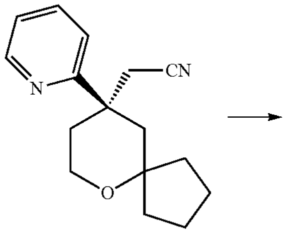

E3

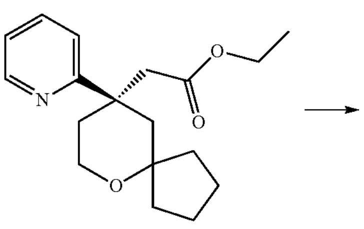

C3-2

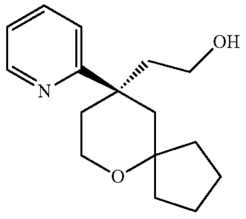

B3

Step 1: the compound E3 (0.78 g, 3.0 mmol, 1.0 equiv) and TsOH·$H_2O$ (628 mg, 3.3 mmol, 1.1 equiv) were added to a flask, and added with anhydrous ethanol (7.8 mL, 10.0 v/w) and water (54 mg, 3.0 mmol, 1.0 equiv). The reaction was refluxed for 8 h. The reaction liquid was evaporated to dryness under reduced pressure. 10 mL of water was added, and the aqueous phase was adjusted to pH 9 with saturated sodium carbonate. The aqueous phase was extracted with methyl tertiary butyl ether (10 mL×2), and the organic phases were combined after spin drying to obtain compound C3-2 (0.84 g, 91.3% yield, 91.2% purity). $^1$H NMR (400 MHz, $CDCl_3$): δ 8.58-8.57 (m, 1H), 7.63 (td, 3J=7.6 Hz, 4J=2.0 Hz, 1H), 7.32 (d, 3J=8.0 Hz, 1H), 7.14-7.10 (m, 1H), 3.87(q, 3J=7.2 Hz, 2H), 3.81-3.78 (m, 2H), 2.83 (d, 2J=14.0 Hz, 1H), 2.57-2.50 (m, 2H), 2.46 (d, 2J =14.0 Hz, 1H), 2.01-1.90 (m, 2H), 1.84-1.79 (m, 1H), 1.72-1.60 (m, 1H), 1.59-1.48 (m, 3H), 1.46-1.34 (m, 1H), 1.22-1.18 (m, 1H), 1.01 (t, 3J=7.2 Hz, 3H) 0.83-0.75 (m, 1H). MS m/z (ESI): 304.2[M+1]$^+$.

Step 2: a compound B3 was prepared with reference to the Step 2 of Example 4.

EXAMPLE 5-1

Preparation of Chiral Alcohol

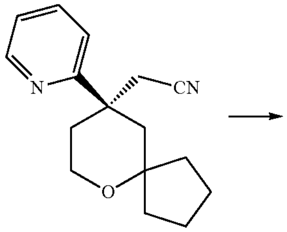

E3

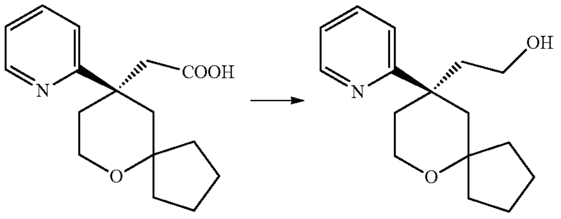

D2 B3

Step 1: the compound E3 (100 g) and water (400 mL) were added to a reaction flask, and the temperature was lowered to 5 to 15° C. 57.4 g of concentrated sulfuric acid was dissolved in 100 mL of water, and the mixture was then added into the reaction flask dropwise. After the addition, the temperature was warmed to 45-50° C., and the mixture was stirred for 1.5 h while keep this temperature. The system was cooled to an internal temperature of 0 to 10° C., 500 mL of toluene was added, and 20% NaOH solution (150 g) was added dropwise. After standing, the liquid was separated, and the aqueous phase was extracted with toluene (500 mL*2) twice, stirring for extraction for 0.5 h each time. After standing, the liquid was separated, and the organic phases were combined. The combined organic phase was washed with saturated NaCl (500 mL), and the organic phase was dried over anhydrous $Na_2SO_4$ and spin-dried to obtain a compound D2 (108 g).

Step 2: a toluene solution (836 g in total) containing the compound D2 (107.4 g) was added into a reaction flask, the internal temperature was cooled to 0 to 10° C., and the nitrogen displacement was performed for three times. Vitride (394.3 g) was slowly added dropwise, and the internal temperature was controlled between 0-10° C. After the dropwise addition, the reaction mixture was warmed to 43° C. and stirred for 1 h. The reaction was cooled to 0-10° C. and quenched with 500 mL water followed by dropwise adding 1500 mL of 20% NaOH solution. The reaction liquid was stirred and extracted with 1000 mL of methyl tertiary butyl ether twice, and the two organic phases were combined. The organic phase was dried over anhydrous $Na_2SO_4$ and filtered, and the filtrate was concentrated under reduced pressure to obtain a compound B3 (91.5 g, yield 89.8%).

EXAMPLE 6

Preparation of Aldehyde

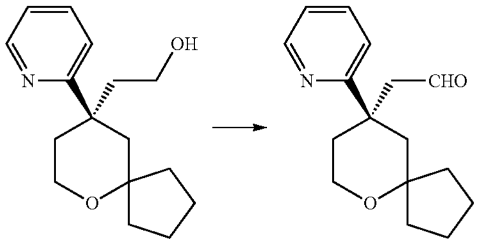

B3 A1

The compound B3 (1.19 g, 4.55 mmol, 1.0 equiv) was added into a 25 mL single-neck bottle, and added with DMSO (6.0 mL, 5.0 v/w) for dissolving until the solution was clear. IBX (3.10 g, 11.4 mmol, 2.5 equiv) was added, and the mixture was stirred at room temperature for 90 min. After confirmation by TLC, a small amount of raw material remained. IBX (0.65 g, 2.27 mmol, 0.5 equiv) was additionally added, while adding additional DMSO (3.6 mL, 3.0 v/w), and the mixture was stirred for 1 h. After it was confirmed through TLC that the raw materials were substantially absent, the reaction liquid was poured into 40 mL of water, and a large amount of solid was precipitated and filtered. The filter cake was washed with 5 mL of water twice. The aqueous phase was adjusted to pH 8-9 with 10% aqueous $Na_2CO_3$. and the aqueous phase was extracted with DCM (15 mL×3). The DCM phase was washed with saturated brine (6 mL×2), and a small amount of solid particles existed in the oily matter after the DCM phase was spin-dried. 5 mL of ethyl acetate was added in the oily matter, and the clear solution was taken and spin-dried to obtain a compound A1 (0.76 g, 64.4% yield, >98.0% purity), MS m/z (ESI): 260.2[M+1]$^+$.

EXAMPLE 7

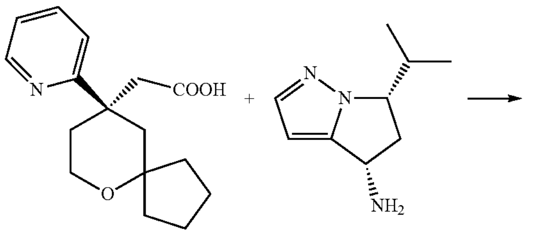

A1 X1-1

-continued

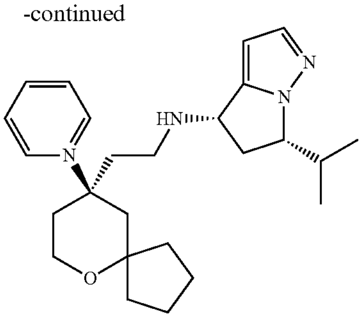

I-1

The compound A1 (50 mg, 0.3 mmol) was dissolved in methanol (5 mL), and the compound X1-1 (78.3 mg, 0.3 mmol) and sodium cyanoborohydride (94 mg, 1.5 mmol) were added. The mixture was stirred for reaction at 20° C. for 3 hours. 20 mL of water was added to the reaction liquid. The mixture was extracted with DCM (30 mL×2), dried over anhydrous sodium sulfate, and concentrated under reduced pressure. The concentrate was purified by the preparative chromatography (preparative column: 21.2×250 mm C18 column, system: 10 mm $NH_4HCO_3$ $H_2O$ wavelength: 254/214 nm, gradient: 30%-60% acetonitrile change) to obtain a monoconfiguration compound I-1 (10.12 mg). MS m/z (ESI):409.2 [M+1]$^+$; $^1$H NMR (400 MHz, $CD_3OD$) δ 8.51 (ddd, J=4.9, 1.8, 0.8 Hz, 1H), 7.79-7.71 (m, 1H), 7.50 (d, J=8.1 Hz, 1H), 7.41 (d, J=1.9 Hz, 1H), 7.22 (ddd, J=7.5, 4.9, 1.0 Hz, 1H), 5.87 (dd, J=1.9, 0.6 Hz, 1H), 4.07 (ddd, J=21.0, 11.7, 6.2 Hz, 2H), 3.81-3.69 (m, 2H), 2.73-2.58 (m, 2H), 2.52 (dd, J=14.0, 2.3 Hz, 1H), 2.48-2.35 (m, 2H), 2.12-1.97 (m, 2H), 1.95-1.82 (m, 2H), 1.78-1.65 (m, 3H), 1.64-1.36 (m, 5H), 1.14-1.04 (m, 1H), 0.99 (d, J=7.0 Hz, 3H), 0.79-0.65 (m, 4H).

EXAMPLE 8

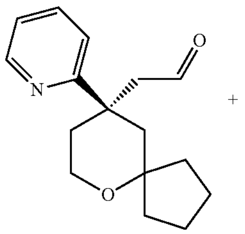

A1

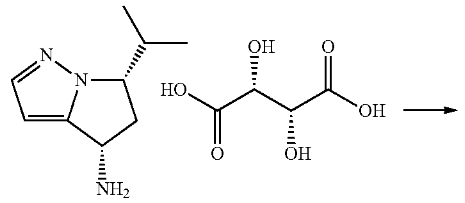

-continued

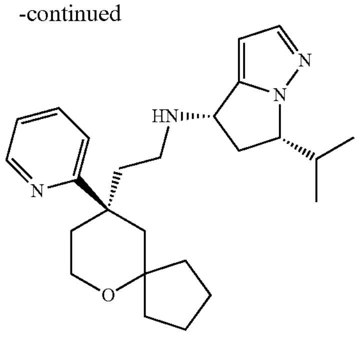

I-1

The compound A1 (950 g), L-tartrate salt of compound X1-1 (1.16 kg), absolute ethanol (7.51 kg), and triethylamine (0.74 kg) were added into a reaction kettle. The system was cooled to 10 to 15° C., sodium triacetoxy borohydride (1.32 kg) was added in batches, and the mixture was further stirred for the reaction for 2 hours. Purified water (38.0 kg) was added into the reaction kettle, and the mixture was stirred for 0.5 hour. An appropriate amount of aqueous hydrochloric acid was slowly added dropwise to the reaction kettle to adjust the pH to about 4.5. 7.04 kg of methyl tertiary ether was added to the reaction kettle. The mixture was stirred for 15 minutes, and stood for separation to collect the aqueous phase. The aqueous phase was adjusted to pH 6.5 by additing an appropriate amount of aqueous sodium carbonate solution. The aqueous phase was extracted with 7.04 kg of methyl tertiary ether twice, and the organic phases were collected and combined. The organic phase was washed with 5.70 kg of purified water, and the liquid was separated. The filtrate was concentrated under reduced pressure to constant weight to obtain a compound I-1 (823 g, yield 55%).

Test Example 1

HTRF-cAMP Cell Assay

Experiment Methods and Steps

I. Cell Resuscitation

1. The resuscitation fluid was removed from a 4° C. refrigerator and placed in a 37° C. water bath for pre-heating for 15 minutes.
2. P6 cells were taken from a liquid nitrogen tank, and the frozen cryopreservation tubes were quickly placed in the 37° C. water bath with gentle shaking for 30 seconds to 1 minute, until it was observed that small ice crystals or the cells were about to melt completely.
3. The tubes were thoroughly disinfected with 70% alcohol and wiped dry.
4. The cryoprotectant was removed by centrifugation, and the cells were resuspended with pre-warmed fresh resuscitation fluid.

a. 3 ml of pre-warmed cell resuscitation fluid was pipetted into a 15 ml centrifuge tube.
b. The centrifuge tube was centrifuged at 1,300 rpm for 3 minutes.
c. The supernatant was removed, and the cells were resuspended with 4 ml of pre-warmed resuscitation fluid.

5. The cell suspension was transferred to a T25 cell culture flask and incubated for 24 hours at 37° C., 5% $CO_2$.
6. After 24 hours of incubation, the resuscitation fluid in the cell culture flask was replaced with a pre-warmed cell culture medium.

II. Cell Passage

1. When the growth density of cells in a T25 culture flask was >70%, the cells were digested and subcultured with a cell digest solution.

a. The culture medium was sucked from the flask, and 4 ml of pre-warmed PBS was added to gently shake and rinse the cells, and the PBS was sucked and discard.
b. 1 ml of cell digest solution was added into the T25 flask.
c. The flask was shaken repeatedly to enable the digest solution completely to cover the flask, and the flask was placed in an incubator containing 5% $CO_2$ at 37° C. for 5 min.
d. The cell culture flask was taken out and the cells were observed under a microscope to observe whether the cells were separated.
e. 3 ml of pre-warmed cell culture medium was added to terminate the digestion.
f. The culture flask was repeatedly and gently rinsed with the cell culture medium to collect the cell suspension into a 15 ml centrifuge tube.
g. The supernatant was removed by centrifugation at 1,300 rpm for 3 minutes. 25 h. The cells were resuspended by 3 ml cell culture medium.

2. The cells were passaged in a ratio of 1:3 (1 ml of cell resuspension+3 ml of cell culture medium were added to each flask and transferred to the T25 flask).

III. Cell Culture Plate

1. The steps 2.2.1 (a-h) were repeated until the cells were passaged to the P8 generation. The cells were counted and resuspended in 2×/1 mM IBMX stimulation buffer to a cell density of $1.2*10^6$/ml.
2. **$1.2*10^6$**/ml of cell solution was seeded, by using a multichannel pipette, in a 384-well plate in a volume of 10 µl per well (i.e., 12,000 cells per well).

IV. c-AMP Assay

1. Relevant reagents and compounds were prepared according to the drug dilution preparation table.

a. 1×Stimulation buffer solution: 1 ml of 5×Stimulation buffer stock solution was added into 4 ml of distilled water, and well mixing.
b. 2×/1 mM IBMX stimulation buffer solution 5 ml: 10 µl of 500 mM IBMX stock solution was added into 4,990 µl of cell culture medium for gently blowing and mixing well.
c. Gradient Dilution Table of Morphine:

| Concentration of stock solution/µM | Gradient high concentration volume (µl) | Stimulation buffer volume (µl) | Diluted concentration/µM | Loading volume of 384-well plate (µl) | Final reaction concentration/µM |
|---|---|---|---|---|---|
| 26606 | — | — | — | — | — |
| gradient | 1 | 19 | 1330.3 | — | — |
| 1) | 2 | 104.4 | 25 | 8 | 10.0000 |
| 2) | 20 | 40 | 8.3333 | 8 | 3.3333 |
| 3) | 20 | 40 | 2.7778 | 8 | 1.1111 |
| 4) | 20 | 40 | 0.9259 | 8 | 0.3704 |

-continued

| Concentration of stock solution/μM | Gradient high concentration volume (μl) | Stimulation buffer volume (μl) | Diluted concentration/μM | Loading volume of 384-well plate (μl) | Final reaction concentration/μM |
|---|---|---|---|---|---|
| 5) | 20 | 40 | 0.3086 | 8 | 0.1235 |
| 6) | 20 | 40 | 0.1029 | 8 | 0.0412 |
| 7) | 20 | 40 | 0.0343 | 8 | 0.0137 |
| 8) | 20 | 40 | 0.0114 | 8 | 0.0046 |
| 9) | 20 | 40 | 0.0038 | 8 | 0.0015 |
| 10) | 20 | 40 | 0.0013 | 8 | 0.0005 |
| 11) | 20 | 40 | 0.0004 | 8 | 0.0002 |

d. Prior to the compound dilution, the compounds were dissolved with DMSO to a stock concentration of 10 mM.

Dilution Table of Compound I-1

| Concentration of stock solution/μM | Gradient high concentration volume (μl) | Stimulation buffer volume (μl) | Diluted concentration/μM | Loading volume of 384-well plate (μl) | Final reaction concentration/μM |
|---|---|---|---|---|---|
| 10000 | — | — | — | — | — |
| 1) | 1 | 399 | 25 | 8 | 10.0000 |
| 2) | 20 | 40 | 8.3333 | 8 | 3.3333 |
| 3) | 20 | 40 | 2.7778 | 8 | 1.1111 |
| 4) | 20 | 40 | 0.9259 | 8 | 0.3704 |
| 5) | 20 | 40 | 0.3086 | 8 | 0.1235 |
| 6) | 20 | 40 | 0.1029 | 8 | 0.0412 |
| 7) | 20 | 40 | 0.0343 | 8 | 0.0137 |
| 8) | 20 | 40 | 0.0114 | 8 | 0.0046 |
| 9) | 20 | 40 | 0.0038 | 8 | 0.0015 |
| 10) | 20 | 40 | 0.0013 | 8 | 0.0005 |
| 11) | 20 | 40 | 0.0004 | 8 | 0.0002 |

e. 50 μM NK477 1 ml: 1 μl of 50 mM NKH477 stock solution was added into 999 μl of 1×Stimulation buffer solution for shaking and mixing well;

f. Detection Reagent

A. cAMP-Cryptate (donor, lyophilized) reaction liquid: 1 ml of 5×cAMP-Cryptate stock solution was added into 4 ml of 1×Lysis & Detection Buffer solution, and gently mixed well.

B. Anti-cAMP-d2 (acceptor, lyophilized) reaction liquid: 1 ml of 5×Anti-cAMP-d2 stock solution was added into 4 ml of 1×Lysis & Detection Buffer solution, and gently mixed well.

2. Steps of cAMP Assay a. cells were seeded at 12,000 cells/well in 10 μl of 2×IBMX stimulation buffer;

b. 8 μl of compound sample diluent was added to each well of cells;

c. 2 μl of prepared 10×NKH 477 solution was added to each well;

d. the cells were incubated for 45 mins at 37° C.;

e. 10 μl of cAMP-d2 and 10 μl of anti-cAMP Cryptate reaction liquid were added;

f. the plates was incubated for 60 mins at room temperature in the dark;

g. the plates were read by HTRF.

3. Detection and Plate Read by RFU

After 60 minutes of incubation, all samples were be detected and read by homogeneous time-resolved fluorescence.

Data Analysis

The data was exported from the corresponding software in the computer connected with the multi-function plate reader, including two signal values of 665 nm and 620 nm. The ratio is calculated as a ratio=665 nm signal value/620 nm signal value×10,000. The data were analyzed by means of the GraphPad Prism software. The best-fit curve was plotted using log (agonist) vs. response. The EC50 values of the compounds were determined by computer-assisted non-linear regression analysis of dose-response curves. PEC50=−logEC50 (EC50 values are in the units of moles); the maximum effect value for % Morphine=(Compound Sample Ratio-Blank Well Ratio)/TOP×100 (Note: the TOP value is the curve Top value fitted by software Graphpad Prism analysis based on the result of the morphine sample ratio—blank well ratio). The results are shown in Table 1.

TABLE 1

Activity of compounds against cAMP

| Compounds | cAMP $EC_{50}$(nM) | cAMP Emax(%) Morphine is 100% |
|---|---|---|
| I-1 | 6.0 | 86.4 |

Test Example 2

β-Arrestin Cell Assay

Experiment Methods and Steps

I. Cell Resuscitation

1. The resuscitation fluid was removed from a 4° C. refrigerator and placed in a 37° C. water bath for pre-heating for 15 minutes.

2. The P6 cells were taken from the liquid nitrogen tank, and the frozen cell culture tubes were quickly placed in a 37° C. water bath with gentle shaking for 30 seconds to 1 minute until small ice crystals were seen or the cells were about to melt completely.

3. The tubes were thoroughly disinfected with 70% alcohol and wiped dry.
4. The cryoprotectant was removed by centrifugation, and the cells were resuspended with pre-warmed fresh resuscitation fluid.

a. 3 ml of pre-warmed cell resuscitation fluid was pipetted into a 15 ml centrifuge tube.
b. The centrifuge tube was centrifuged at 1,300 rpm for 3 minutes.
c. The supernatant was removed, and the cells were resuspended with 4 ml of pre-warmed resuscitation fluid.

5. The cell suspension was transferred to a T25 cell culture flask and incubated for 24 hours at 37° C., 5% $CO_2$.
6. After 24 hours of incubation, the resuscitation fluid in the cell culture flask was replaced with a pre-warmed cell culture medium.

II. Cell Passage

1. When the growth density of cells in a T25 culture flask was >70%, the cells were digested and subcultured with a cell digest solution.

a. The culture medium was sucked from the flask, and 4 ml of pre-warmed PBS was added to gently shake and rinse the cells, and the PBS was sucked and discard.
b. 1 ml of cell digest solution was added into the T25 flask.
c. The flask was shaken repeatedly to enable the digest solution completely to cover the flask, and the flask was placed in an incubator containing 5% $CO_2$ at 37° C. for 5 min.
d. The cell culture flask was taken out and the cells were observed under a microscope to observe whether the cells were separated.
e. 3 ml of pre-warmed cell culture medium was added to terminate the digestion.
f. The culture flask was repeatedly and gently rinsed with the cell culture medium to collect the cell suspension into a 15 ml centrifuge tube.
g. The supernatant was removed by centrifugation at 1,300 rpm for 3 minutes.
h. The cells were resuspended by 3 ml cell culture medium.

2. The cells were passaged in a ratio of 1:3 (1 ml of cell resuspension+3 ml of cell culture medium were added to each flask and transferred to the T25 flask).
3. The steps 2.2.1 (a-h) were repeated until the cells were passaged through the P8 generation.

III. Cell Culture Plate 1. 20 μl of the cell suspension was taken using pipette, and the number of the cells was determined with a cell counter.
2. The cells were centrifugated at 1,300 rpm for 3 minutes to obtain cell pellets. p1 3. The supernatant was removed, and the corresponding cell plating solution was added to adjust the cell concentration to $2\times10^5$/ml.
4. $2\times10^5$/ml of cell solution was seeded, by using a multichannel pipette and according to the experimental design, in a 384-well plate in a volume of 10 μl per well (i.e., 4,000 cells per well).
5. The cell-seeded 384-well plate was placed into an incubator containing 5% $CO_2$ at 37° C. for 24 h.

IV. β-Arrestin Assay

1. The compounds were prepared according to the following dilution table.

a. Gradient Dilution Table of Morphine:

| Concentration of stock solution/μM | Gradient high concentration volume (μl) | Plating Buffer adding volume (μl) | Volume of added DMSO (μl) | Diluted concentration/ μM | Loading volume of 384-well plate (μl) | Final reaction concentration/ μM |
|---|---|---|---|---|---|---|
| 26606 | — | — | — | — | — | — |
| Prepare | 2 | 18 | 0 | 2660.6 | — | — |
| A | 2 | 101.763 | 2.661 | 50.000 | 5 | 10.000 |
| B | 20 | 39 | 1 | 16.667 | 5 | 3.333 |
| C | 20 | 39 | 1 | 5.556 | 5 | 1.111 |
| D | 20 | 39 | 1 | 1.852 | 5 | 0.370 |
| E | 20 | 39 | 1 | 0.617 | 5 | 0.123 |
| F | 20 | 39 | 1 | 0.206 | 5 | 0.041 |
| G | 20 | 39 | 1 | 0.069 | 5 | 0.014 |
| H | 20 | 39 | 1 | 0.023 | 5 | 0.005 |

b. Prior to the compound dilution, the compounds were dissolved with DMSO to a stock concentration of 10 mM.

Dilution Table of Compound I-1:

| Concentration of stock solution/μM | Gradient high concentration volume (μl) | Volume of added DMSO (μl) | Diluted concentration./ μM | Volume of diluted solution (μl) | Add Plating Buffer volume (μl) | Final diluted concentration./ μM | Loading volume of 384-well plate (μl) | Final reaction concentration/ μM |
|---|---|---|---|---|---|---|---|---|
| 10000 | — | — | — | — | — | — | — | — |
| A | 12.5 | 50 | 2000 | 2.5 | 97.5 | 50.000 | 5 | 10.000 |
| B | 20 | 40 | 666.667 | 2.5 | 97.5 | 16.667 | 5 | 3.333 |
| C | 20 | 40 | 222.222 | 2.5 | 97.5 | 5.556 | 5 | 1.111 |
| D | 20 | 40 | 74.074 | 2.5 | 97.5 | 1.852 | 5 | 0.370 |

-continued

| Dilution Table of Compound I-1: | | | | | | | | |
|---|---|---|---|---|---|---|---|---|
| Concentration of stock solution/μM | Gradient high concentration volume (μl) | Volume of added DMSO (μl) | Diluted concentration./ μM | Volume of diluted solution (μl) | Add Plating Buffer volume (μl) | Final diluted concentration./ μM | Loading volume of 384-well plate (μl) | Final reaction concentration/ μM |
| E | 20 | 40 | 24.691 | 2.5 | 97.5 | 0.617 | 5 | 0.123 |
| F | 20 | 40 | 8.230 | 2.5 | 97.5 | 0.206 | 5 | 0.041 |
| G | 20 | 40 | 2.743 | 2.5 | 97.5 | 0.069 | 5 | 0.014 |
| H | 20 | 40 | 0.914 | 2.5 | 97.5 | 0.023 | 5 | 0.005 |

2. 5 μl of each compound sample dilution prepared above was added to the 384-well plate.
3. After the addition of the samples was complete, the 384-well plate was placed into the incubator containing 5% $CO_2$ at 37° C. for 90 minutes.

V. RLU Detection

1. Before the end of compound incubation, a working detection solution was prepared according to the following proportion (protected from light). Then, 12.5 μl of the working detection solution was added to each well. The plate was protected from light, and incubated for 1 h at room temperature on a shaker.

| Ingredients | Proportioning |
|---|---|
| Cell Assay Buffer | 19 |
| Substrate Reagent 1 | 5 |
| Substrate Reagent 2 | 1 |
| Total Volume | 25 |

2. At the end of compound incubation, 12.5 μl of the above working solution was added to each well. The plate was protected from light, and incubated for 1 h at room temperature on an 80 rpm shaker.
3. At the end of incubation, the plates were read using a multi-function plate reader.

Data Analysis

The data were exported from the corresponding software in the computer connected with the multi-function plate reader, and analyzed by means of the GraphPad Prism software. The best-fit curve was plotted using log (agonist) vs. response, the EC50 values of the compounds were determined by computer-assisted non-linear regression analysis of dose-response curves. PEC50=−logEC50 (EC50 values are in units of moles). The maximum effect valued of % morphine=(RLU values of compound samples−RLU values of blank wells)/TOP×100 (Note: the TOP value is the curve Top value fitted by software Graphpad Prism analysis based on the result of the RLU value of the morphine sample−the RLU value of the blank well). The results are shown in Table 2.

TABLE 2

| Test results of compounds on β-arrestin | |
|---|---|
| Compounds | β-arrestin Emax(%) Morphine is 100% |
| I-1 | 1.3 |

Table 1 and Table 2 reveal that the compound I-1 has a higher inhibitory activity against cAMP and a higher Emax value, and has a lower Emax value against β-arrestin, having good bias.

The literature mentioned in the present disclosure are incorporated herein by reference as if each literature was individually cited for reference. Furthermore, those skilled in the art, upon reading the above description, can make various changes and modifications to the present disclosure, and these equivalents shall also fall within the scope of the appended claims.

What is claimed is:

1. A compound represented by Formula B or a stereoisomer thereof,

B

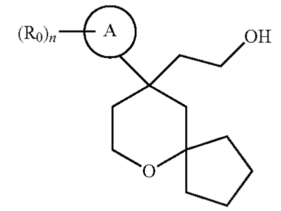

wherein:

the ring A is a $C_{6-10}$ aromatic ring, or a five-or six-membered monocyclic heteroaryl ring;

$(R_0)_n$ represents that hydrogen on the ring A is substituted by n $R_0$ groups, where n is 0, 1, 2, 3, or 4; the n $R_0$ groups are identical or different and are each independently hydrogen, cyano, acetyl, hydroxyl, hydroxymethyl, hydroxyethyl, carboxyl, halogenated $C_{1-8}$ alkyl, halogen, nitro, $C_{6-10}$ aryl, five-or six-membered monocyclic heteroaryl, $C_{1-8}$ alkyl, $C_{1-8}$ alkoxyl, $C_{3-6}$ cycloalkyl, $C_{3-6}$ cycloalkoxyl, $C_{2-4}$ alkenyl, $C_{2-4}$ alkynyl, $NR_{11}R_{12}$,—$CONR_{11}R_{12}$,—$C(O)OC_{1-8}$ alkyl, $C_{1-8}$ alkyl,—$SO_2C_{1-8}$ alkyl —$SO_2C_{6-10}$ aryl, —$COC_{6-10}$ aryl (—CO-phenyl), a four-to six-membered saturated monoheterocyclic ring, or a three-to six-membered saturated monocyclic ring, wherein the $C_{6-10}$ aryl, the five-or six-membered monocyclic heteroaryl, the four-to six-membered saturated monoheterocyclic ring, and the three-to six-membered saturated monocyclic ring are each unsubstituted or substituted by one, two, or three substituents selected from the group consisting of acetyl, hydroxyl, cyano, halogen, $C_{1-3}$ alkyl, $C_{1-3}$ alkoxyl, $C_{3-6}$ cycloalkyl, and $NR_{11}R_{12}$; and $R_{11}$ and $R_{12}$ are each independently hydrogen, $C_{1-8}$ alkyl, halogenated $C_{1-8}$ alkyl, $C_{3-6}$ cycloalkyl, or a four-to six-membered saturated monoheterocyclic ring; or $R_{11}$ and $R_{12}$ together with the nitrogen atom linked thereto form a four-to six-membered saturated monoheterocyclic ring, wherein the four-to six-membered saturated monoheterocyclic ring is unsubstituted or substituted with one, two, or three $C_{1-4}$ alkyl groups.

2. The compound or the stereoisomer thereof according to claim 1, wherein the compound represented by Formula B has a structure represented by Formula B2:

B2

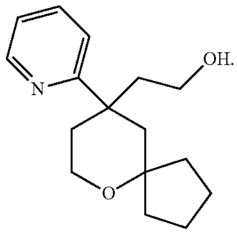

3. The compound or the stereoisomer thereof according to claim 1, wherein the compound represented by Formula B has a structure represented by Formula B3:

B3

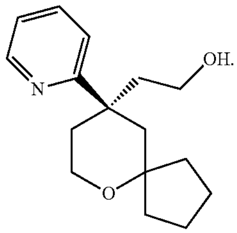

4. A preparation method of the compound represented by Formula B or the stereoisomer thereof according to claim 1, comprising the following step of:

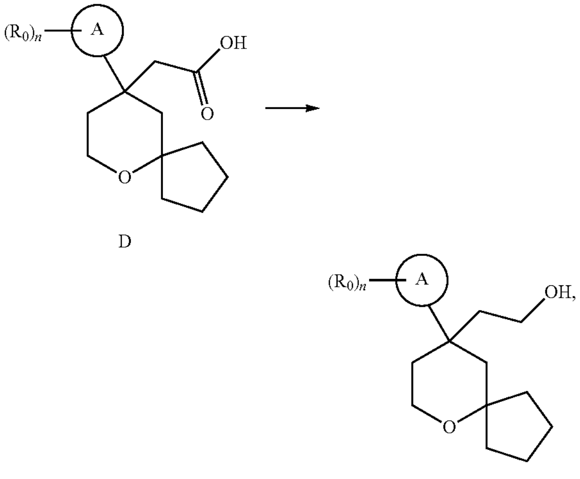

D

B reacting a compound represented by Formula D or a stereoisomer thereof to obtain the compound represented by Formula B or the stereoisomer thereof, wherein the ring A and $(R_0)_n$ are as defined in claim 1.

5. The preparation method according to claim 4, wherein the compound represented by Formula B has a structure represented by Formula B1:

B1

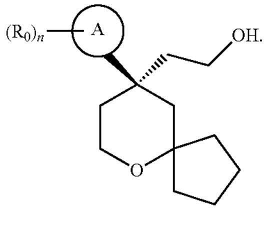

6. The preparation method according to claim 4, wherein the compound represented by Formula D or the stereoisomer thereof is prepared with a method comprising:

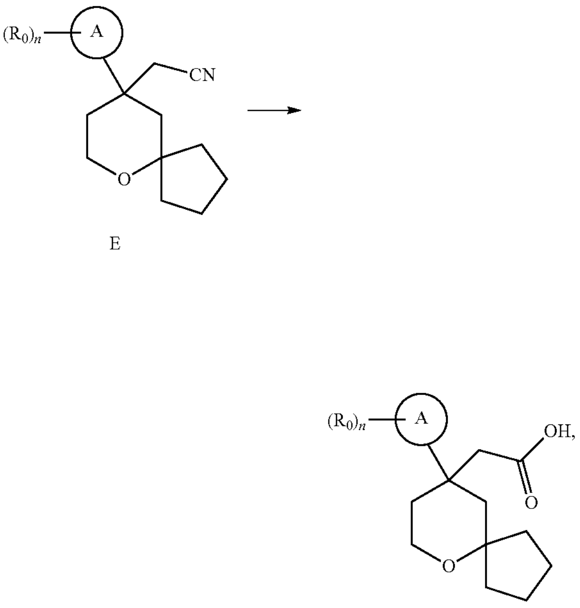

E

D reacting a compound represented by Formula E or a stereoisomer thereof to obtain the compound represented by Formula D or the stereoisomer thereof.

7. A preparation method of a compound represented by Formula X or a stereoisomer thereof, comprising the steps of:

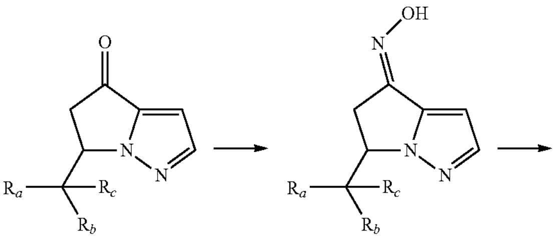

Z Y

-continued

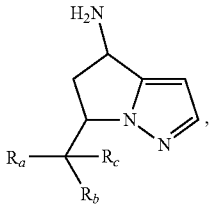

X reacting a compound represented by Formula Z or a stereoisomer thereof to obtain a compound represented by Formula Y or a stereoisomer thereof; and reacting the compound represented by Formula Y or the stereoisomer thereof to obtain the compound represented by Formula X or the stereoisomer thereof, wherein, in Formula Z, Formula Y, and Formula X:

$R_a$ and $R_b$ are each independently hydrogen, halogen, $C_{1-6}$ alkyl, halogenated $C_{1-6}$ alkyl, or halogenated $C_{1-6}$ alkoxyl; or $R_a$ and $R_b$ together with the carbon atom linked thereto form a four-to six-membered saturated monoheterocyclic ring or a three-to six-membered saturated monocyclic ring, wherein the four-to six-membered saturated monoheterocyclic ring and the three-to six-membered saturated monocyclic ring are each unsubstituted or substituted by one, two, or three substituents selected from the group consisting of cyano, hydroxyl, hydroxymethyl, cyanomethyl, halogen, $C_{1-3}$ alkoxyl, $C_{1-3}$ alkyl, —$COC_{1-3}$ alkyl, —$CONR_{a1}R_{b1}$, $NR_{a1}R_{b1}$, —$NHCOC_{1-3}$ alkyl, —$NHCONR_{a1}R_{b1}$, —$NHSO_2C_{1-3}$ alkyl, —$NHSO_2NR_{a1}R_{b1}$, and —$NHSO_2C_{3-6}$ cycloalkyl;

$R_c$ is hydrogen, halogen, $C_{1-6}$ alkyl, $C_{2-6}$ alkenyl, $C_{2-6}$ alkynyl, $C_{1-6}$ alkoxyl, halogenated $C_{1-6}$ alkyl halogenated $C_{1-6}$ alkoxyl, —$COC_{1-6}$ alkyl, —$CONR_{a1}R_{b1}$, $NR_{a1}R_{b1}$, —$NHCOC_{1-6}$ alkyl, —$NHCONR_{a1}R_{b1}$, —$NHSO_2C_{1-3}$ alkyl, —$NHSO_2NR_{a1}R_{b1}$, —$NHSO_2C_{3-6}$ cycloalkyl, —$SO_2C_{1-3}$ alkyl, —$SO_2NR_{a1}R_{b1}$, a four-to six-membered saturated monoheterocyclic ring, $C_{6-10}$ aryl, or a five-or six-membered monocyclic heteroaryl, wherein the four-to six-membered saturated monoheterocyclic ring, the $C_{6-10}$ aryl, and the five-or six-membered monocyclic heteroaryl are each unsubstituted or substituted by one, two, or three substituents selected from the group consisting of cyano, hydroxyl, hydroxymethyl, cyanomethyl, halogen, $C_{1-3}$ alkoxyl, $C_{1-3}$ alkyl, —$COC_{1-3}$ alkyl, —$CONR_{a1}R_{b1}$, $NR_{a1}R_{b1}$, —$NHCOC_{1-3}$ alkyl, —$NHCONR_{a1}Rb_1$, —$NHSO_2C_{1-3}$ alkyl, —$NHSO_2NR_{a1}R_{b1}$, and —$NHSO_2C_{3-6}$ cycloalkyl; and $R_{a1}$ and $R_{b1}$ are each independently hydrogen, $C_{1-6}$ alkyl, halogenated $C_{1-6}$ alkyl, $C_{3-6}$ cycloalkyl, or a four-to six-membered saturated monoheterocyclic ring; or $R_{a1}$ and $R_{b1}$ together with the nitrogen atom linked thereto form a four-to six-membered saturated monoheterocyclic ring, wherein the four-to six-membered saturated monoheterocyclic ring is unsubstituted or substituted with one, two, or three $C_{1-3}$ alkyl groups.

8. The preparation method according to claim 7, wherein the compound represented by Formula X has a structure represented by Formula X1:

X1

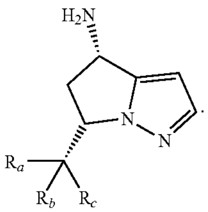

9. The preparation method according to claim 8, wherein a compound represented by Formula XI is prepared by the following step of:

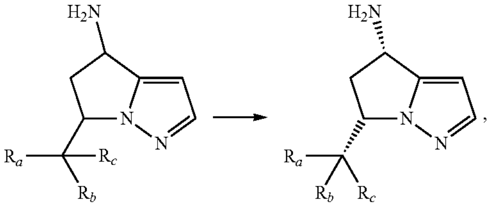

X X1 performing a chiral resolution on the compound represented by Formula X to obtain the compound represented by Formula XI.

10. The preparation method according to claim 7, wherein:

$R_a$ is methyl, $R_b$ is H, and $R_c$ is methyl.

11. The preparation method according to claim 9, wherein a resolving agent used in the chiral resolution is L-tartaric acid, L-dibenzoyl tartaric acid, L-malic acid, L-mandelic acid, L-camphorsulfonic acid, or (S)-(+)-1, 1'-Binaphthyl-2,2'-diylhydrogenphosphate.

12. A preparation method of a compound represented by Formula I or a stereoisomer thereof, comprising the following steps of:

(i) reacting a compound represented by Formula B or a stereoisomer thereof to obtain a compound represented by Formula A or a stereoisomer thereof:

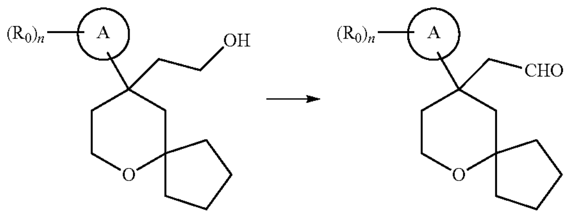

;

B A (ii) reacting the compound represented by Formula A or the stereoisomer thereof with a compound represented by Formula X or a stereoisomer thereof to obtain the compound represented by Formula I or the stereoisomer thereof:

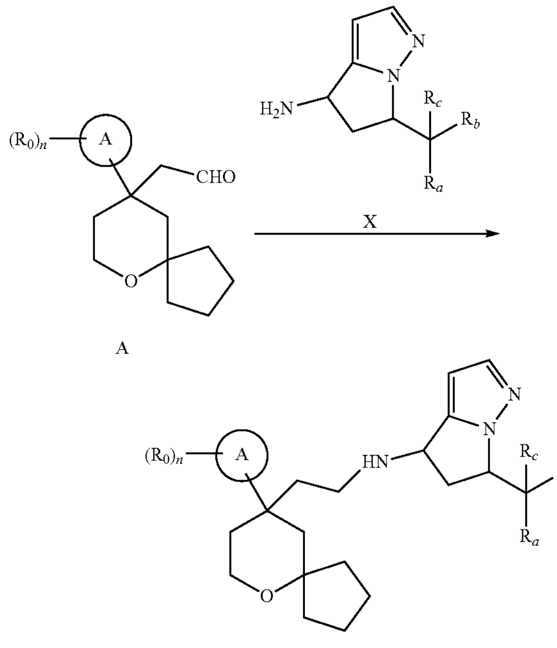

A

I wherein:

the ring A is a $C_{6-10}$ aromatic ring or a five-or six-membered monocyclic heteroaryl ring;

$(R_0)_n$ represents that hydrogen on the ring A is substituted by n $R_0$ groups, where n is 0, 1, 2, 3, or 4; the n $R_0$ groups are identical or different and are each independently hydrogen, cyano, acetyl, hydroxyl, hydroxymethyl, hydroxyethyl, carboxyl, halogenated $C_{1-8}$ alkyl, halogen, nitro, $C_{6-10}$ aryl, five-or six-membered monocyclic heteroaryl, $C_{1-8}$ alkyl, $C_{1-8}$ alkoxyl, $C_{3-6}$ cycloalkyl, $C_{3-6}$ cycloalkoxyl, $C_{2-4}$ alkenyl, $C_{2-4}$ alkynyl, $NR_{11}R_{12}$, —$CONR_{11}R_{12}$,—$C(O)OC_{1-8}$ alkyl, —OC(O)$C_{1-8}$ alkyl, —$SO_2C_{1-8}$ alkyl, —$SO_2C_{6-10}$ aryl, —$COC_{6-10}$ aryl (—CO-phenyl), a four-to six-membered saturated monoheterocyclic ring, or a three-to six-membered saturated monocyclic ring, wherein the $C_{6-10}$ aryl, the five-or six-membered monocyclic heteroaryl, the four-to six-membered saturated monoheterocyclic ring, and the three-to six-membered saturated monocyclic ring are each unsubstituted or substituted by one, two, or three substituents selected from the group consisting of acetyl, hydroxyl, cyano, halogen, $C_{1-3}$ alkyl, $C_{1-3}$ alkoxyl, $C_{3-6}$ cycloalkyl, and $NR_{11}R_{12}$;

$R_{11}$ and $R_{12}$ are each independently hydrogen, $C_{1-8}$ alkyl halogenated $C_{1-8}$ alkyl, $C_{3-6}$ cycloalkyl, or a four-to six-membered saturated monoheterocyclic ring; or $R_{11}$ and $R_{12}$ together with the nitrogen atom linked thereto form a four-to six-membered saturated monoheterocyclic ring, wherein the four-to six-membered saturated monoheterocyclic ring is unsubstituted or substituted with one, two, or three $C_{1-4}$ alkyl groups;

$R_a$ and $R_b$ are each independently hydrogen, halogen, $C_{1-6}$ alkyl, halogenated $C_{1-6}$ alkyl, or halogenated $C_{1-6}$ alkoxyl; or $R_a$ and $R_b$ together with the carbon atom linked thereto form a four-to six-membered saturated monoheterocyclic ring or a three-to six-membered saturated monocyclic ring, wherein the four-to six-membered saturated monoheterocyclic ring and the three-to six-membered saturated monocyclic ring are each unsubstituted or substituted by one, two, or three substituents selected from the group consisting of cyano, hydroxyl, hydroxymethyl, cyanomethyl, halogen, $C_{1-3}$ alkoxyl, $C_{1-3}$ alkyl, —$COC_{1-3}$ alkyl, —$CONR_{a1}R_{b1}$, $NR_{a1}R_{b1}$, —$NHCOC_{1-3}$ alkyl, —$NHCONR_{a1}R_{b1}$, —$NHSO_2C_{1-3}$ alkyl, —$NHSO_2NR_{a1}R_{b1}$, and —$NHSO_2C_{3-6}$ cycloalkyl;

$R_c$ is hydrogen, halogen, $C_{1-6}$ alkyl, $C_{2-6}$ alkenyl, $C_{2-6}$ alkynyl, $C_{1-6}$ alkoxyl, halogenated $C_{1-6}$ alkyl, halogenated $C_{1-6}$ alkoxyl, —$COC_{1-6}$ alkyl, —$CONR_{a1}R_{b1}$, $NR_{a1}R_{b1}$, —$NHCOC_{1-6}$ alkyl, —$NHCONR_{a1}R_{b1}$, —$NHSO_2C_{1-3}$ alkyl, —$NHSO_2NR_{a1}R_{b1}$, —$NHSO_2C_{3-6}$ cycloalkyl, —$SO_2C_{1-3}$ alkyl, —$SO_2NR_{a1}R_{b1}$, a four-to six-membered saturated monoheterocyclic ring, $C_{6-10}$ aryl, ora five-or six-membered monocyclic heteroaryl, wherein the four-to six-membered saturated monoheterocyclic ring, the $C_{6-10}$ aryl, and the five-or six-membered monocyclic heteroaryl are each unsubstituted or substituted by one, two, or three substituents selected from the group consisting of cyano, hydroxyl, hydroxymethyl, cyanomethyl, halogen, $C_{1-3}$ alkoxyl, $C_{1-3}$ alkyl, —$COC_{1-3}$ alkyl, —$CONR_{a1}R_{b1}$, $NR_{a1}R_{b1}$, —$NHCOC_{1-3}$ alkyl, —$NHCONR_{a1}R_{b1}$, —$NHSO_2C_{1-3}$ alkyl, —$NHSO_2NR_{a1}R_{b1}$, and —$NHSO_2C_{3-6}$ cycloalkyl; and $R_{a1}$ and $R_{b1}$ are each independently hydrogen, $C_{1-6}$ alkyl, halogenated $C_{1-6}$ alkyl, $C_{3-6}$ cycloalkyl, or a four-to six-membered saturated monoheterocyclic ring; or $R_{a1}$ and $R_{b1}$ together with the nitrogen atom linked thereto form a four-to six-membered saturated monoheterocyclic ring, wherein the four-to six-membered saturated monoheterocyclic ring is unsubstituted or substituted with one, two, or three $C_{1-3}$ alkyl groups.

13. The preparation method according to claim 12, wherein the compound represented by Formula B or the stereoisomer thereof is prepared with a preparation method of a compound represented by Formula B or a stereoisomer thereof, the method comprising the following step of:

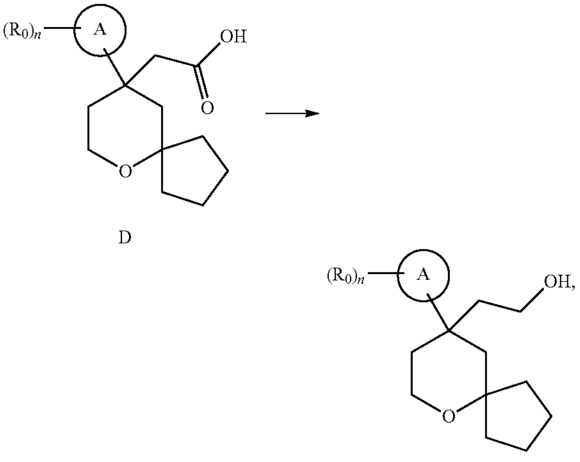

D

B reacting a compound represented by Formula D or a stereoisomer thereof to obtain the compound represented by Formula B or the stereoisomer thereof.

14. The preparation method according to claim 12, wherein the compound represented by Formula X or the stereoisomer thereof is prepared with a preparation method of a compound represented by Formula X or a stereoisomer thereof, comprising the steps of:

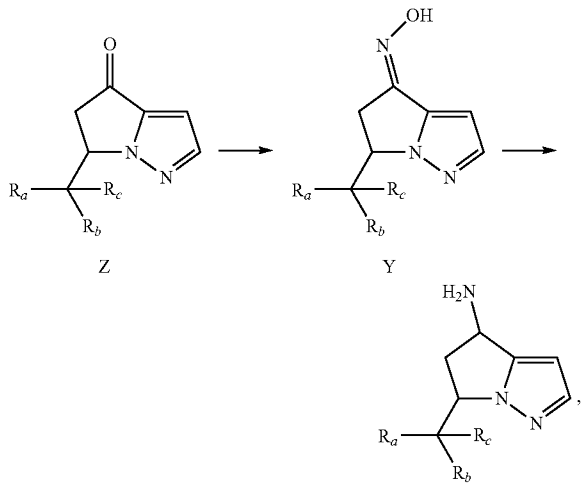

Z Y X reacting a compound represented by Formula Z or a stereoisomer thereof to obtain a compound represented by Formula Y or a stereoisomer thereof; and reacting the compound represented by Formula Y or the stereoisomer thereof to obtain the compound represented by Formula X or the stereoisomer thereof.

15. The preparation method according to claim 12, wherein the compound represented by Formula I has a structure represented by Formula I-1:

I-1

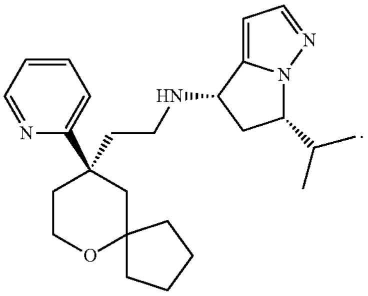

16. The preparation method according to claim 15, wherein the compound represented by Formula 1-1 is prepared according to the following synthetic route:

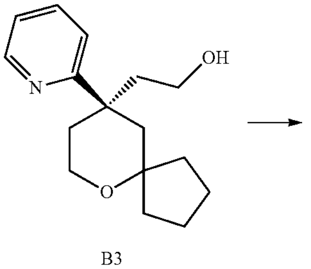

B3

-continued

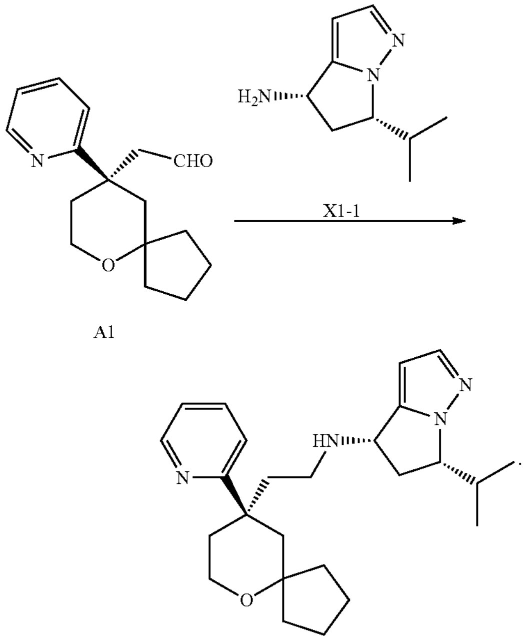

A1

I-1

17. The preparation method according to claim 16, wherein the compound represented by Formula X1-1 is selected from a free base of the compound represented by Formula X1-1, or an L-tartrate, L-dibenzoyltartrate, L-malate, L-mandelate, L-camphorsulfonate or(S)-(+)-1,1'-Binaphthyl-2,2'-diyl hydrogenphosphate salt of the compound represented by Formula X1-1.

18. The preparation method according to claim 16, wherein the compound represented by Formula B3 is prepared according to the following synthetic route:

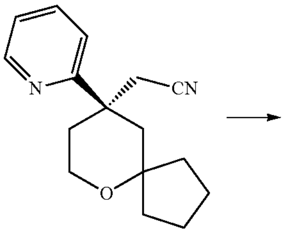

E3

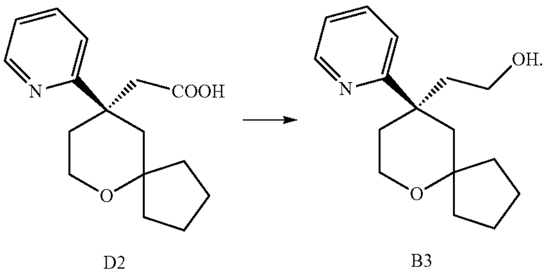

D2 B3

19. A compound represented by Formula Y or a stereoisomer thereof:

Y

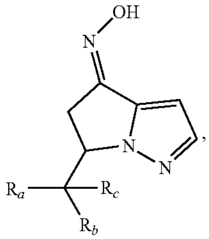

, wherein:

$R_a$ and $R_b$ are each independently hydrogen, halogen, $C_{1-6}$ alkyl, halogenated $C_{1-6}$ alkyl, or halogenated $C_{1-6}$ alkoxyl; or halogenated $C_{1-6}$; $R_a$ and $R_b$ together with the carbon atom linked thereto form a four-to six-membered saturated monoheterocyclic ring or a three-to six-membered saturated monocyclic ring, wherein the four-to six-membered saturated monoheterocyclic ring and the three-to six-membered saturated monocyclic ring are each unsubstituted or substituted by one, two, or three substituents selected from the group consisting of cyano, hydroxyl, hydroxymethyl, cyanomethyl, halogen, $C_{1-3}$ alkoxyl, $C_{1-3}$ alkyl, —$COC_{1-3}$ alkyl, —$CONR_{a1}R_{b1}$, $NR_{a1}R_{b1}$, —$NHCOC_{1-3}$ alkyl, —$NHCONR_{a1}R_{b1}$, —$NHSO_2C_{1-3}$ alkyl, —$NHSO_2NR_{a1}R_{b1}$, and —$NHSO_2C_{3-6}$ cycloalkyl;

$R_c$ is hydrogen, halogen, $C_{1-6}$ alkyl, $C_{2-6}$ alkenyl, $C_{2-6}$ alkynyl, $C_{1-6}$ alkoxyl, halogenated $C_{1-6}$ alkyl halogenated $C_{1-6}$ alkoxyl, —$COC_{1-6}$ alkyl, —$CONR_{a1}R_{b1}$, $NR_{a1}R_{b1}$, —$NHCOC_{1-6}$ alkyl —$NHCONR_{a1}R_{b1}$, —$NHSO_2C_{1-3}$ alkyl, —$NHSO_2NR_{a1}R_{b1}$, —$NHSO_2C_{3-6}$ cycloalkyl, —$SO_2C_{1-3}$ alkyl, —$SO_2NR_{a1}R_{b1}$, a four-to six-membered saturated monoheterocyclic ring, $C_{6-10}$ aryl, or five-or six-membered monocyclic heteroaryl, wherein the four-to six-membered saturated monoheterocyclic ring, the $C_{6-10}$ aryl, and the five-or six-membered monocyclic heteroaryl are each unsubstituted or substituted by one, two, or three substituents selected from the group consisting of cyano, hydroxyl, hydroxymethyl, cyanomethyl, halogen, $C_{1-3}$ alkoxyl, $C_{1-3}$ alkyl, —$COC_{1-3}$ alkyl, —$CONR_{a1}R_{b1}$, $NR_{a1}R_{b1}$, —$NHCOC_{1-3}$ alkyl, —$NHCONR_{a1}R_{b1}$, —$NHSO_2C_{1-3}$ alkyl, —$NHSO_2NR_{a1}R_{b1}$, and —$NHSO_2C_{3-6}$ cycloalkyl;

$R_{a1}$ and $R_{b1}$ are each independently hydrogen, $C_{1-6}$ alkyl, halogenated $C_{1-6}$ alkyl, $C_{3-6}$ cycloalkyl or a four-to six-membered saturated monoheterocyclic ring; or $R_{a1}$ and $R_{b1}$ together with the nitrogen atom linked thereto form a four-to six-membered saturated monoheterocyclic ring, wherein the four-to six-membered saturated monoheterocyclic ring is unsubstituted or substituted with one, two, or three $C_{1-3}$ alkyl groups.

20. The compound or the stereoisomer thereof according to claim 19, wherein the represented by Formula Y is a compound represented by Formula Y-1:

Y-1

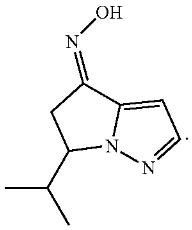

.

* * * * *